(12) United States Patent
Ahmed et al.

(10) Patent No.: US 8,372,831 B2
(45) Date of Patent: Feb. 12, 2013

(54) ISOXAZOLINE LINKED PYRROLO[2,1-C][1,4]BENZODIAZEPINE HYBRIDS AS POTENTIAL ANTICANCER AGENTS AND THE PROCESS FOR PREPARATION THEREOF

(75) Inventors: Kamal Ahmed, Hyderabad (IN); Jonnala Surendranadha Reddy, Hyderabad (IN); Dudekula Dastagiri, Hyderabad (IN); Earla Vijaya Bharathi, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 78 days.

(21) Appl. No.: 12/934,594

(22) PCT Filed: Oct. 31, 2008

(86) PCT No.: PCT/IN2008/000713
§ 371 (c)(1),
(2), (4) Date: Jan. 18, 2011

(87) PCT Pub. No.: WO2009/118748
PCT Pub. Date: Oct. 1, 2009

(65) Prior Publication Data
US 2011/0118237 A1    May 19, 2011

(30) Foreign Application Priority Data
Mar. 26, 2008 (IN) .............. 785/DEL/2008

(51) Int. Cl.
C07D 487/04    (2006.01)
A61K 31/5517    (2006.01)
A61P 35/00    (2006.01)

(52) U.S. Cl. ........................ 514/220; 540/496
(58) Field of Classification Search .................. 540/496; 514/220
See application file for complete search history.

(56) References Cited

FOREIGN PATENT DOCUMENTS
WO    2005/063759 A1    7/2005
WO    2006/070380 A1    7/2006
WO    2008/020455 A2    2/2008

OTHER PUBLICATIONS

Gregson et al. "Design, Synthesis, and Evaluation of a Novel Pyrrolobenzodiazepine DNA-Interactive Agent with Highly Efficient Cross-Linking Ability and Potent Cytotoxicity." J. Med. Chem. 2001, 44, 737-748.
Hurley et al. "Pyrrolo (1,4) benzodiazepine antitumor antibiotics. In vitro interaction of anthramycin, sibiromycin and tomaymycin with DNA using specifically radiolabelled molecules." Biochim Biophys Acta. Apr. 4, 1977; 475(3):521-535.
Kamal et al. "Design, Synthesis, and Evaluation of a New Noncross-Linking Pyrrolobenzodiazepine Dimers with Efficient DNA Binding Ability and Potent Antitumor Activity." J. Med. Chem. 2002, 45, 4679-4688.
Kamal et al. "Synthesis of Novel C2 and C2-C8 Linked Pyrrolo[2,1-c][1,4]benzodiazepine-napthalinnide Hybrids as DNA-Binding Agents." Bioorganic & Medicinal Chemistry Letters 13 (2003) 3577-3581.
Kamal et al. "Synthesis and biological activity of fluoroquinolone-pyrrolo[2,1-c][1,4] benzodiazepine conjugates." Bioorganic & Medicinal Chemistry Letters. Mar. 15, 2005; 13(6):2021-9.
Kaplan et al. "Anthramycin binding to deoxyribonucleic acid-mitomycin C complexes. Evidence for drug-induced deoxyribonucleic acid conformational change and cooperativity in mitomycin C binding." Biochemistry. Dec. 22, 1998; 20(26):7572-80.
Kohn et al. "Reaction of anthramycin with deoxyribonucleic acid." J. Mol. Biol. Aug. 1970; 51(3):551-72.
Kunimoto et al. "Mazethramycin, a new member of anthramycin group antibiotics." J Antibiot (Tokyo). Jun. 1980; 33 (6):665-7.
Simoni et al. "Heterocyclic and Phenyl Double-Bond-Locked Combretastatin Analogues Possessing Potent Apoptosis-Inducing Activity in HL60 and in MDR Cell Lines." J. Med. Chem. 2005, 48, 723-736.
Thurston et al. "Synthesis of Sequence-Selectiv C8-Linked Pyrrolo[2,1-c][1,4]benzodiazepine DNA Interstrand Cross-Linking Agents." J. Org. Chem. 1996, 61, 8141-8147.

Primary Examiner — Bruck Kifle
(74) Attorney, Agent, or Firm — K&L Gates LLP

(57) ABSTRACT

The present invention provides compounds of general formula (5a-d) and (9a-h) useful as potential antitumour agents against human cancer cell lines. The present invention also provides a process for the preparation of pyrrolo [2,1-c][1,4] benzodiazepine hybrids of general formula (5a-d) and (9a-h).

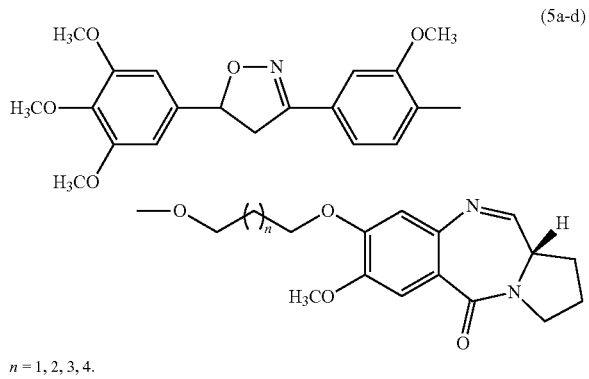

$n$ = 1, 2, 3, 4.

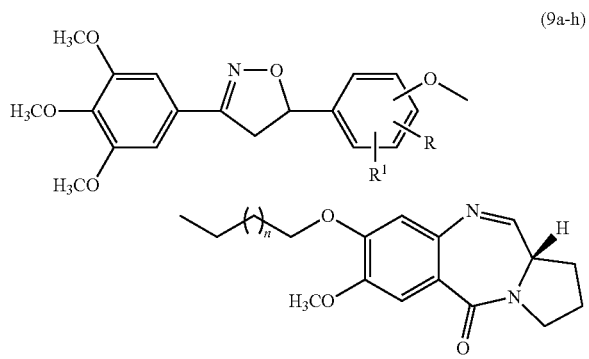

$n$ = 1, 2, 3, 4.
R = 4-OCH$_3$, R$^1$ = 5-H
R = 3-OCH$_3$, R$^1$ = 5-OCH$_3$

23 Claims, No Drawings

ISOXAZOLINE LINKED PYRROLO[2,1-C][1,4]BENZODIAZEPINE HYBRIDS AS POTENTIAL ANTICANCER AGENTS AND THE PROCESS FOR PREPARATION THEREOF

CROSS REFERENCE TO RELATED APPLICATIONS

The present application is an application under 35 U.S.C. 371 of International Patent Application No. PCT/IN2008/000713 filed Oct. 31, 2008, which claims priority to Indian Patent Application No. 785/DEL/2008 filed Mar. 26, 2008, the entire contents of both of which are hereby incorporated by reference in their entirety.

FIELD OF THE INVENTION

The present invention relates to isoxazoline linked pyrrolo[2,1-c][1,4]benzodiazepine hybrids and a process for the preparation there of. More particularly it relates to (11aS)-7-(methyloxy)-8-(n-[(2-(methyloxy)-4-5-[3,4,5-tri(methyloxy)phenyl]-4-,5-dihydro-3-isoxadolylphenyl)oxy]alkyloxy)-2,3,5,11a-tetrahydro-1H benzo[e]pyrrolo[1,2-a][1,4]diazepi-5-one, (11aS)-8-(n-2,6-dimethoxy-4-[3-(3,4,5-trimethoxyphenyl)-4,5-dihydro-5-isoxazolyl] phenoxyalkyloxy)-7-methoxy-2,3,5,11a-tetrahydro-1H-benzo[e]pyrrolo[1,2-a][1,4]diazepin-5-one with aliphatic chain length variations useful as anticancer (antitumour) agent. The structural formula of these isoxazoline-linked pyrrolo[2,1c][1,4]benzodiazepine hybrids are given below.

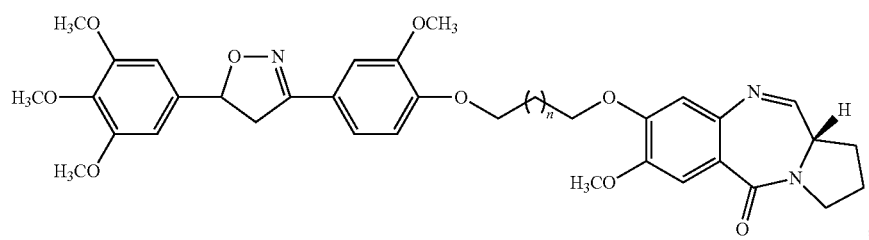

$n = 1, 2, 3, 4$.

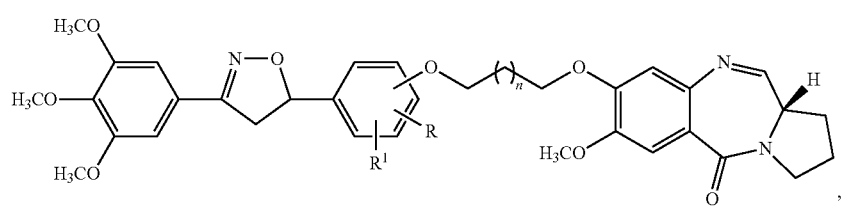

$n = 1, 2, 3, 4$.
$R = 4\text{-OCH}_3, R^1 = 5\text{-H}$
$R = 3\text{-OCH}_3, R^1 = 5\text{-OCH}_3$

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551; Hurley, L. H.; Gairpla, C. and Zmijewski, M. Biochem. *Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. *J. Org. Chem.* 1996, 61, 8141).

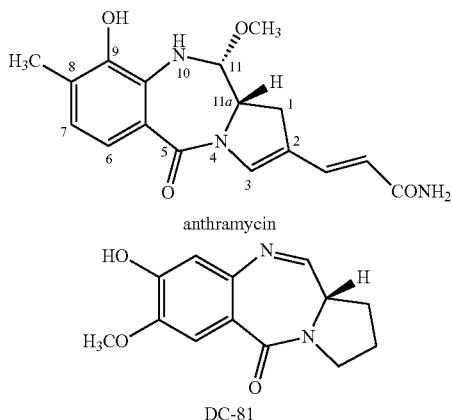

anthramycin

DC-81

Formula 5a-d

Formula 9a-h

-continued

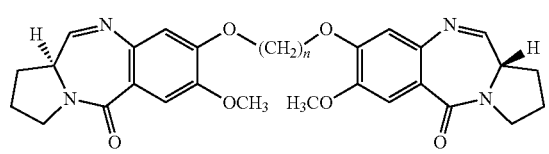

DC-81 dimers ($n = 3$-5); DSB-120 ($n = 3$)

-continued

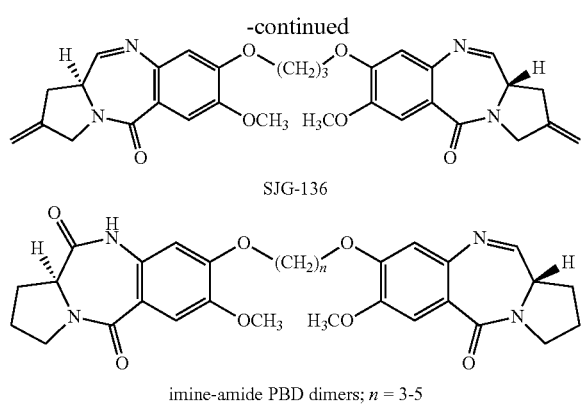

SJG-136 imine-amide PBD dimers; n = 3-5

Recently, PBD dimers have been synthesized that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). on-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have also been synthesized that have significant DNA binding ability and potent antitumour activity. (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardiotoxicity, development of drug resistance and metabolic inactivation.

OBJECTIVES OF THE INVENTION

The main objective of the present invention is to provide novel isoxazoline linked pyrrolo[2,1-c][1,4]benzodiazepine hybrids, useful as antitumour agents.

Yet another objective of this invention is to provide a process for the preparation of novel isoxazoline linked pyrrolo[2,1-c][1,4]benzodiazepine hybrids.

SUMMARY OF THE INVENTION

Accordingly the present invention provides a novel isoxazoline linked pyrrolo[2,1-c][1,4]benzodiazepine hybrid of general formula A

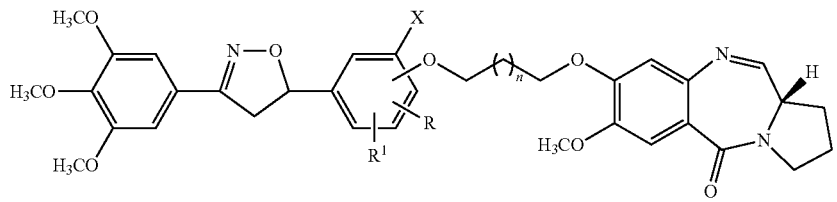

R = H or 4-OCH$_3$, or 3-OCH$_3$,
R$^1$ = H or 5-H or 5-OCH$_3$
X = H or OCH$_3$

In an embodiment of the present invention the novel isoxazoline linked pyrrolo[2,1-c][1,4]benzodiazepine hybrid of general formula A comprises the compounds of general formula 5 and 9.

Formula 5a-d

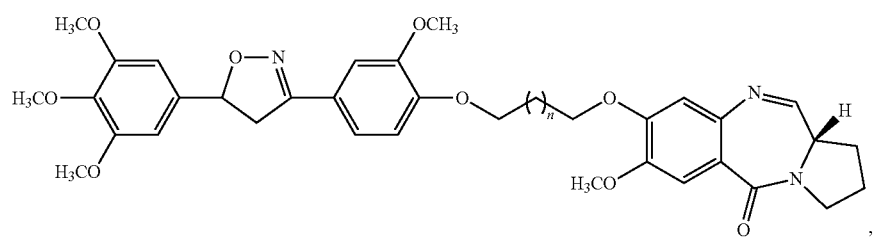

n = 1, 2, 3, 4.

-continued

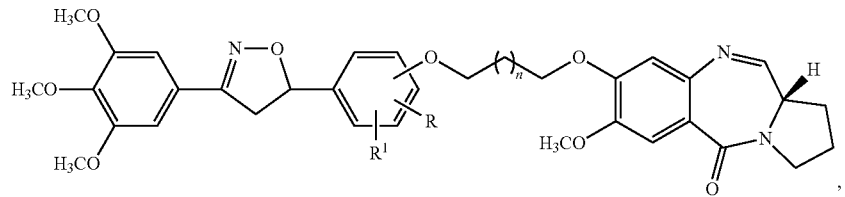

Formula 9a-h n = 1, 2, 3, 4.
R = 4-OCH₃, R¹ = 5-H
R = 3-OCH₃, R¹ = 5-OCH₃

In an embodiment of the present invention the novel isoxazoline linked pyrrolo[2,1-c][1,4]benzodiazepine hybrid according to claim 1 is represented by the group of the following compounds:

(11aS)-7-(methyloxy)-8-(3-[(2-(methyloxy)-4-5-[3,4,5-tri(methyloxy)phenyl]-4-,5-dihydro-3-isoxazolylphenyl)oxy]propyloxy)-2,3,5,11a-tetrahydro-1H benzo[e]pyrrolo[1,2-a][1,4]diazepi-5-one (5a);

(11aS)-7-(methyloxy)-8-(4-[(2-(methyloxy)-4-5-[3,4,5-tri(methyloxy)phenyl]-4,5-dihydro-3-isoxazolylphenyl)oxy]butyloxy)-2,3,5,11a-tetrahydro-1H benzo[e]pyrrolo[1,2-a][1,4]diazepin-5-one (5b);

(11aS)-7-(methyloxy)-8-(5-[(2-(methyloxy)-4-5-[3,4,5-tri(methyloxy)phenyl]-4,5-dihydro-3-isoxazolylphenyl)oxy]pentyloxy)-2,3,5,11a-tetrahydro-1H benzo[e]pyrrolo[1,2-a][1,4]diazepi-5-one (5c);

(11aS)-7-(methyloxy)-8-(6-[(2-(methyloxy)-4-5-[3,4,5-tri(methyloxy)phenyl]-4,5-dihydro-3-isoxazolylphenyl)oxy]hexyloxy)-2,3,5,11a-tetrahydro-1H benzo[e]pyrrolo[1,2-a][1,4]diazepi-5-one (5d);

(11aS)-7-(methyloxy)-8-(3-[(2-(methyloxy)-5-3-[2,3,4-tri(methyloxy)phenyl]-4,5-dihydro-5-isoxazolylphenyl)oxy]propyloxy)-2,3,5,11a-tetrahydro-1H-benzo[e]pyrrolo[1,2-a][1,4]diazepin-5-one (9a);

(11aS)-7-(methyloxy)-8-(4-[(2-(methyloxy)-5-3-[2,3,4-tri(methyloxy)phenyl]-4,5-dihydro-5-isoxazolylphenyl)oxy]butyloxy)-2,3,5,11a-tetrahydro-1H-benzo[e]pyrrolo[1,2-a][1,4]diazepin-5-one (9b);

(11aS)-7-(methyloxy)-8-(5-[(2-(methyloxy)-5-3-[2,3,4-tri(methyloxy)phenyl]-4,5-dihydro-5-isoxazolylphenyl)oxy]pentyloxy)-2,3,5,11a-tetrahydro-1H-benzo[e]pyrrolo[1,2-a][1,4]diazepin-5-one (9c);

(11aS)-7-(methyloxy)-8-(6-[(2-(methyloxy)-5-3-[2,3,4-tri(methyloxy)phenyl]-4,5-dihydro-5-isoxazolylphenyl)oxy]hexyloxy)-2,3,5,11a-tetrahydro-1H-benzo[e]pyrrolo[1,2-a][1,4]diazepin-5-one (9d);

(11aS)-8-(3-[(2,6-di(methyloxy)-4-3-[2,3,4-tri(methyloxy)phenyl]-4,5-dihydro-5-isoxazolylphenyl)oxy]propyloxy)-7-(methyloxy)-2,3,5,11a-tetrahydro-1H-benzo[e]pyrrolo[1,2-a][1,4]diazepin-5-one (9e);

(11aS)-8-(4-[(2,6-di(methyloxy)-4-3-[2,3,4-tri(methyloxy)phenyl]-4,5-dihydro-5-isoxazolylphenyl)oxy]butyloxy)-7-(methyloxy)-2,3,5,11a-tetrahydro-1H-benzo[e]pyrrolo[1,2-a][1,4]diazepin-5-one (9f);

(11aS)-8-(5-[(2,6-di(methyloxy)-4-3-[2,3,4-tri(methyloxy)phenyl]-4,5-dihydro-5-isoxazolylphenyl)oxy]pentyloxy)-7-(methyloxy)-2,3,5,11a-tetrahydro-1H-benzo[e]pyrrolo[1,2-a][1,4]diazepin-5-one (9g);

(11aS)-8-(6-[(2,6-di(methyloxy)-4-3-[2,3,4-tri(methyloxy)phenyl]-4,5-dihydro-5-isoxazolylphenyl)oxy]hexyloxy)-7-(methyloxy)-2,3,5,11a-tetrahydro-1H-benzo[e]pyrrolo[1,2-a][1,4]diazepin-5-one (9h);

In yet another embodiment the structural formula of the representative compounds of isoxazoline linked pyrrolo[2,1-c][1,4]benzodiazepine hybrids are:

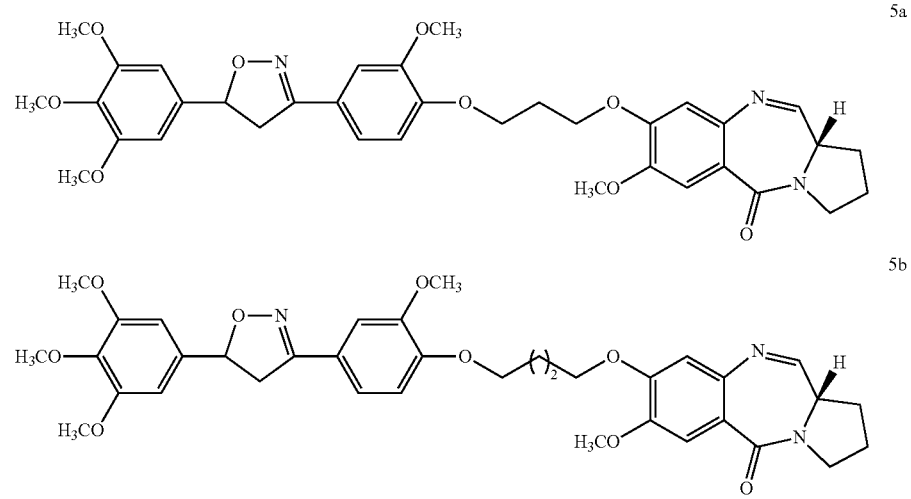

-continued
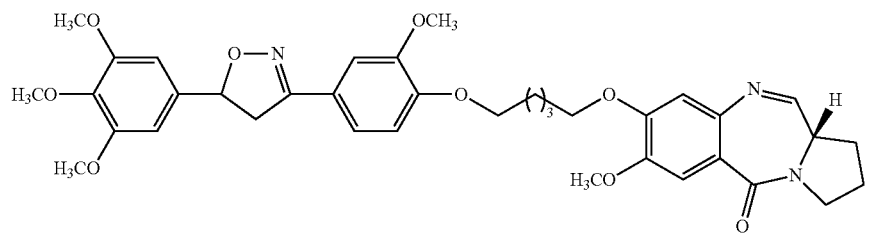
5c
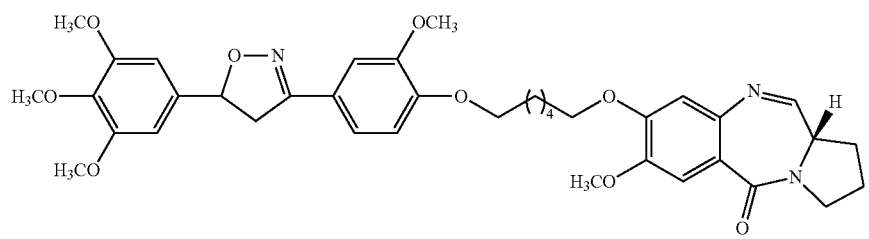
5d
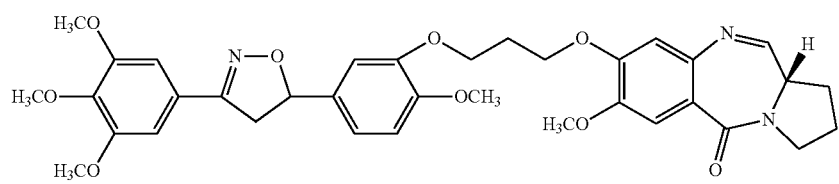
9a
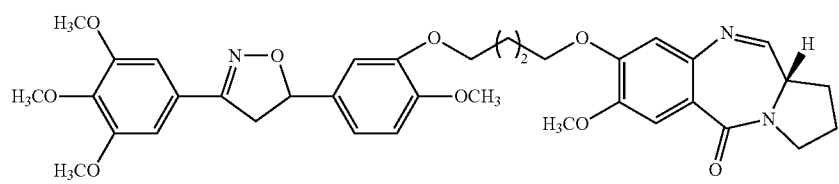
9b
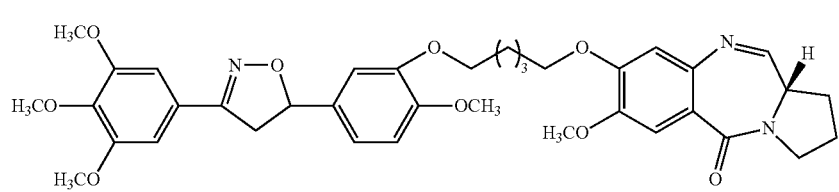
9c
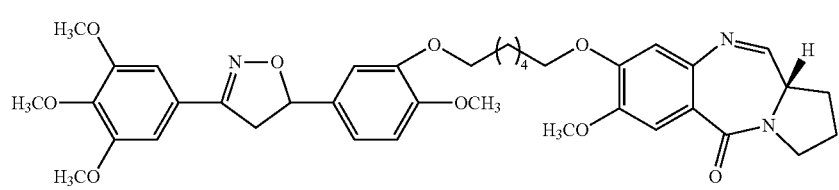
9d
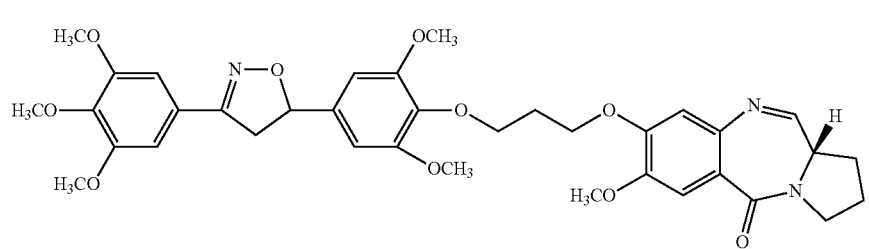
9e

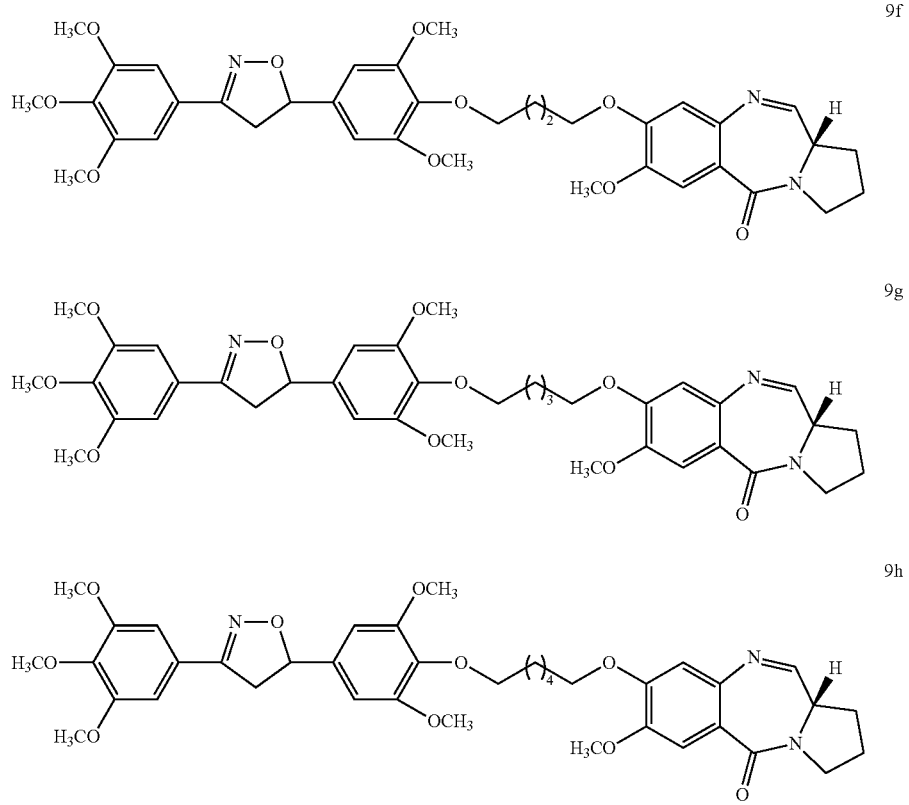

In yet another embodiment the novel isoxazoline linked pyrrolo[2,1-c][1,4]benzodiazepine hybrids exhibit an in vitro anticancer/antitumour activity against human cancer cell lines selected from the group consisting of lung (Hop-62, NCI-H226, NCI-H522), leukemia (K-562, SR), colon (HCT-116, HCT-15, HCC-2998), CNS(SF-539), melanoma (SK-MEL-5, UACC-62, M14), ovarian (IGROV1), renal (A498), prostate (PC3) breast (BT-549, MDA-MB-435, HS578T) cell lines.

In yet another embodiment the concentration of isoxazoline linked pyrrolo[2,1-c][1,4]benzodiazepine hybrids (5b and 9b), used for in vitro activity against lung for GI50 is in the range of 0.12 to 0.24 and 0.60 to 3.68 µM respectively, an exposure period of at least 48 hrs.

In yet another embodiment the concentration of isoxazoline linked pyrrolo[2,1-c][1,4]benzodiazepine hybrids (5b and 9b) used for in vitro activity against leukemia for GI50 is in the range of 0.12 to 0.46 and 1.12 to 1.90 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against colon for GI50 is in the range of 0.18 to 0.36 and 1.55 to 2.75 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against CNS for GI50 is in the range of 022 to 0.34 and 1.71 to 1.96 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against melanoma for GI50 is in the range of 0.16 to 0.27 and 1.47 to 2.88 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against ovarian for GI50 is in the range of 0.24 to 0.47 and 1.57 to 3.37 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against renal for GI50 is in the range of 0.18 to 0.30 and 1.39 to 3.51 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against prostate for GI50 is in the range of 0.32 to 0.33 0.58 to 2.48 µM respectively, at an exposure period of at least 48 hrs.

In yet another embodiment the concentration of isoxazoline linked pyrrolo[2,1-c][1,4]benzodiazepine hybrids (5b and 9b) used for in vitro activity against breast for GI50 is in the range of 0.09 to 0.28 and 1.10 to 3.54 µM respectively, at an exposure period of at least 48 hrs.

The present invention further provides a pharmaceutical composition comprising isoxazoline linked pyrrolo[2,1-c][1,4]benzodiazepine hybrid, its derivatives, analogues, salts or mixture thereof optionally with pharmaceutically acceptable carriers, adjuvants and additives.

In yet another embodiment the isoxazoline linked pyrrolo[2,1-c][1,4]benzodiazepine hybrids used are represented by a general formula 5 and 9.

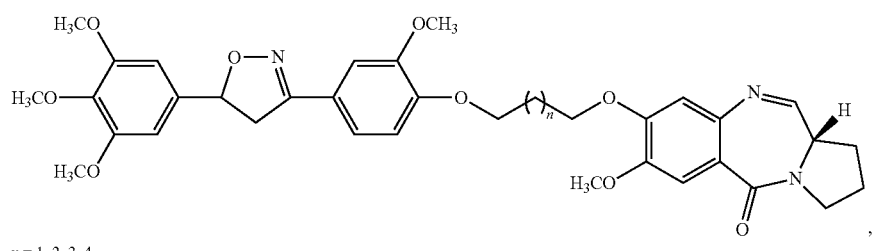

Formula 5a-d n = 1, 2, 3, 4.

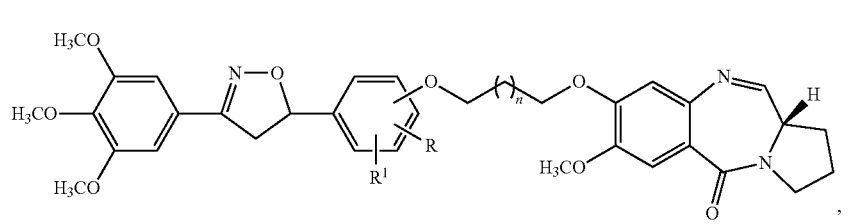

Formula 9a-h n = 1, 2, 3, 4.
R = 4-OCH₃, R¹ = 5-H
R = 3-OCH₃, R¹ = 5-OCH₃

The present invention further provides a process for the preparation of isoxazoline linked pyrrolo[2,1-c][1,4]benzodiazepine hybrids of formula A

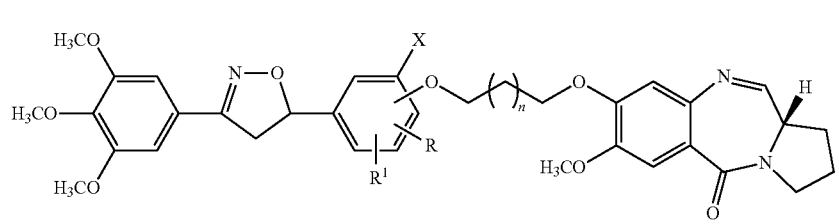

Formula A

R = H or 4-OCH₃, or 3-OCH₃,
R¹ = H or 5-H or 5-OCH₃
X = H or OCH₃ the said process comprising the steps of:
a) reacting (2S)—N-[(n-bromoalkyloxy)-3-methoxy-2-nitrobenzoyl)]pyrrolidine-2-carboxaldehyde diethylthioacetal of formula 1

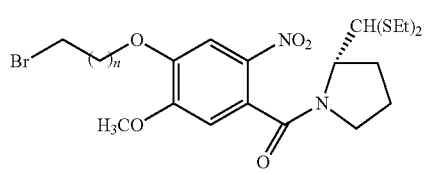

1a-d

With isoxazoline derivatives selected from the compounds of formulas 2 and 6

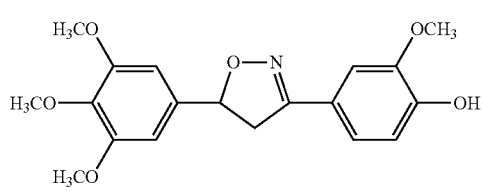

2

-continued

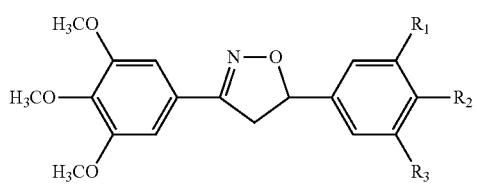

6

(i) R₁ = OH, R₂ = OCH₃, R₃ = H
(ii) R₁ = OCH₃, R₂ = OH, R₃ = OCH₃ in an aprotic water miscible organic solvent, in the presence of anhydrous mild inorganic base, under refluxing temperature in an oil bath, for a period of about 24 to 48 hrs, followed by the removal of inorganic base by filtration and evaporating the organic solvent to obtain the resultant crude product and purifying it by column chromatography to obtain the desired products of formulae 3a-d and 7a-h.

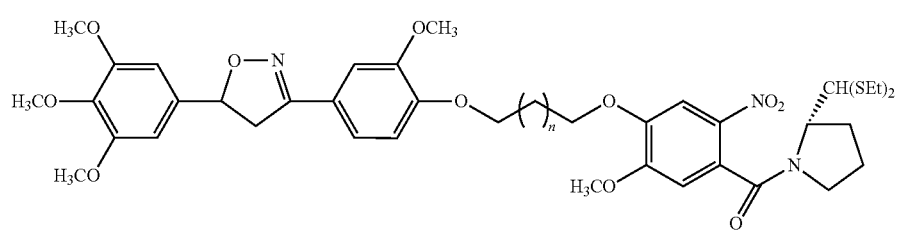

3a-d

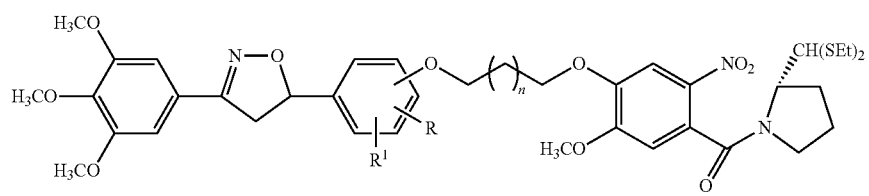

7a-h

R = 4-OCH₃, R¹ = 5-H
R = 3-OCH₃, R¹ = 5-OCH₃ n = 1, 2, 3, 4 b) reducing the compounds of formula 3a-d and 7a-h with $SnCl_2.2H_2O$, in an alcohol, under reflux, followed by the evaporation of alcohol and adjusting the pH of the resultant product layer to about 8 to 9 by using a base of the kind sodium bicarbonate and potassium bicarbonate of, followed by extraction with ethyl acetate and washing the combined organic phase with brine solution and evaporating the solvent to obtain the desired products of formula 4a-d and 8a-h respectively.

4a-d

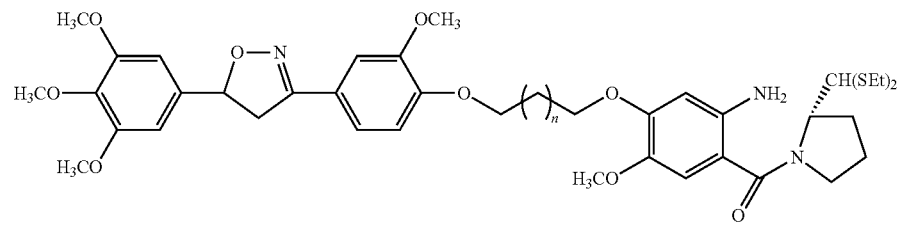

8a-h

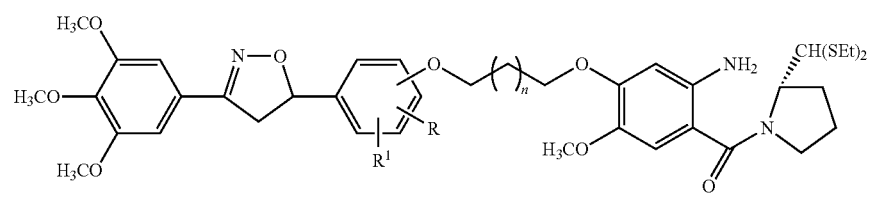

R = 4-OCH₃, R¹ = 5-H
R = 3-OCH₃, R¹ = 5-OCH₃
n = 1-4 c) reacting the above said amino compounds of formula 4 and 8 obtained in step (b) with a deprotecting agent of the kind of mercuric chloride by known method to obtain the desired compound of formula 5 and 9.

Formula 5a-d

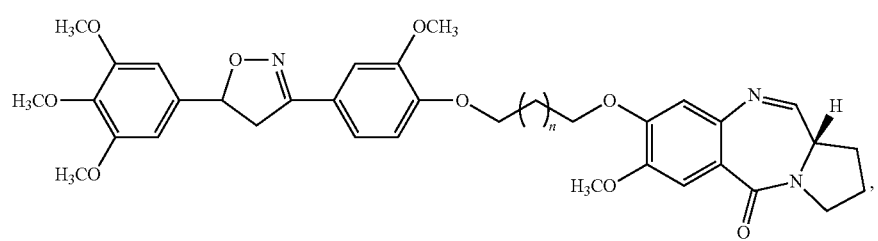

n = 1, 2, 3, 4.

Formula 9a-h

R = 4-OCH$_3$, R$^1$ = 5-H
R = 3-OCH$_3$, R$^1$ = 5-OCH$_3$
n = 1, 2, 3, 4.

In yet another embodiment the mild inorganic base used in steps (a) is potassium carbonate.

In yet another embodiment the aprotic organic solvent used in step (a) is acetone and acetonitrile In yet another embodiment the organic solvent used in step (c) is acetonitrile and acetone In yet another embodiment the alcohol used in step (b) is selected from methanol and ethanol.

In yet another embodiment the compounds of formula 5a-d and 9a-h. obtained are represented by a group of the following compounds:

(11aS)-7-(methyloxy)-8-(3-[(2-(methyloxy)-4-5-[3,4,5-tri(methyloxy)phenyl]-4-,5-dihydro-3-isoxazolylphenyl)oxy]propyloxy)-2,3,5,11a-tetrahydro-1H benzo[e]pyrrolo[1,2-a][1,4]diazepi-5-one (5a);

(11aS)-7-(methyloxy)-8-(4-[(2-(methyloxy)-4-5-[3,4,5-tri(methyloxy)phenyl]-4,5-dihydro-3-isoxazolylphenyl)oxy]butyloxy)-2,3,5,11a-tetrahydro-1H benzo[e]pyrrolo[1,2-a][1,4]diazepin-5-one (5b);

(11aS)-7-(methyloxy)-8-(5-[(2-(methyloxy)-4-5-[3,4,5-tri(methyloxy)phenyl]-4,5-dihydro-3-isoxazolylphenyl)oxy]pentyloxy)-2,3,5,11a-tetrahydro-1H benzo[e]pyrrolo[1,2-a][1,4]diazepi-5-one (5c);

(11aS)-7-(methyloxy)-8-(6-[(2-(methyloxy)-4-5-[3,4,5-tri(methyloxy)phenyl]-4,5-dihydro-3-isoxazolylphenyl)oxy]hexyloxy)-2,3,5,11a-tetrahydro-1H benzo[e]pyrrolo[1,2-a][1,4]diazepi-5-one (5d);

(11aS)-7-(methyloxy)-8-(3-[(2-(methyloxy)-5-3-[2,3,4-tri(methyloxy)phenyl]-4,5-dihydro-5-isoxazolylphenyl)oxy]propyloxy)-2,3,5,11a-tetrahydro-1H-benzo[e]pyrrolo[1,2-a][1,4]diazepin-5-one (9a);

(11aS)-7-(methyloxy)-8-(4-[(2-(methyloxy)-5-3-[2,3,4-tri(methyloxy)phenyl]-4,5-dihydro-5-isoxazolylphenyl)oxy]butyloxy)-2,3,5,11a-tetrahydro-1H-benzo[e]pyrrolo[1,2-a][1,4]diazepin-5-one (9b);

(11aS)-7-(methyloxy)-8-(5-[(2-(methyloxy)-5-3-[2,3,4-tri(methyloxy)phenyl]-4,5-dihydro-5-isoxazolylphenyl)oxy]pentyloxy)-2,3,5,11a-tetrahydro-1H-benzo[e]pyrrolo[1,2-a][1,4]diazepin-5-one (9c);

(11aS)-7-(methyloxy)-8-(6-[(2-(methyloxy)-5-3-[2,3,4-tri(methyloxy)phenyl]-4,5-dihydro-5-isoxazolylphenyl)oxy]hexyloxy)-2,3,5,11a-tetrahydro-1H-benzo[e]pyrrolo[1,2-a][1,4]diazepin-5-one (9d);

(11aS)-8-(3-[(2,6-di(methyloxy)-4-3-[2,3,4-tri(methyloxy)phenyl]-4,5-dihydro-5-isoxazolylphenyl)oxy]propyloxy)-7-(methyloxy)-2,3,5,11a-tetrahydro-1H-benzo[e]pyrrolo[1,2-a][1,4]diazepin-5-one (9e);

(11aS)-8-(4-[(2,6-di(methyloxy)-4-3-[2,3,4-tri(methyloxy)phenyl]-4,5-dihydro-5-isoxazolylphenyl)oxy]butyloxy)-7-(methyloxy)-2,3,5,11a-tetrahydro-1H-benzo[e]pyrrolo[1,2-a][1,4]diazepin-5-one (9f);

(11aS)-8-(5-[(2,6-di(methyloxy)-4-3-[2,3,4-tri(methyloxy)phenyl]-4,5-dihydro-5-isoxazolylphenyl)oxy]pentyloxy)-7-(methyloxy)-2,3,5,11a-tetrahydro-1H-benzo[e]pyrrolo[1,2-a][1,4]diazepin-5-one (9g);

(11aS)-8-(6-[(2,6-di(methyloxy)-4-3-[2,3,4-tri(methyloxy)phenyl]-4,5-dihydro-5-isoxazolylphenyl)oxy]hexyloxy)-7-(methyloxy)-2,3,5,11a-tetrahydro-1H-benzo[e]pyrrolo[1,2-a][1,4]diazepin-5-one (9h);

In still another embodiment the isoxazoline linked pyrrolo[2,1-c][1,4]benzodia-zepine hybrids of formula 5a-d and 9a-h, exhibit an in vitro anticancer/antitumour activity against human cancer cell lines selected from the group consisting of lung, leukemia, colon, CNS, melanoma, ovarian, renal, prostate, and breast cell lines.

DETAILED DESCRIPTION OF THE INVENTION

The present invention provides a process for preparation of pyrrolo[2,1-c][1,4]benzodiazepine hybrids of formula 5a-d and 9 a-h of the drawing accompanying the specification where n=1-4 which comprises reacting the Isoxazoline compounds formula 2 and 6 with (2S)—N-[n-bromo-alkyloxy)-3-methoxy-2-nitrobenzoyl)]pyrrolidine-2-carboxaldehyde diethylthioacetal of formula 1 in presence of CH$_3$COCH$_3$/K$_2$CO$_3$ for a period of 48 h with isolating the compounds of formula 3 and 7 by conventional methods. Reducing the above nitro compound of formula 3 and 7 with SnCl$_2$.2H$_2$O in presence of organic solvent with reflux temperature, resulting the compounds of formulae 4 and 8 with known deprotecting agents in a conventional manner to give novel pyrrolo[2,1-c][1,4]benzodiazepine hybrids of formula 5 and 9, where 'n' is as stated above The precursors, 4-(4,5-dihydro-5-(3,4,5-trimethoxyphenyl)isoxazol-3-yl)-2-methoxy-phenol of formula 2 (1. Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; Dicristina, A.; Dusonchet, L.; Meli, M.; Tolomeo, M. J. Med. Chem. 2005, 48, 723) and (2S)—N-(4-hydroxy-5-methoxy-2-nitrobenzoyl)pyrrolidine-2-carboxaldehyde diethylthio acetal of formula 1 (Thurston, D. E.; Morris, S. J.; Hartley, J. A. Chem. Commun. 1996, 563-565) have been prepared by literature methods.

Some representative compounds of formula 5a-d and 9a-h. for the present inventions are given below (11aS)-7-(methyloxy)-8-(3-[(2-(methyloxy)-4-5-[3,4,5-tri(methyloxy)phenyl]-4-, 5-dihydro-3-isoxazolylphenyl)oxy]propyloxy)-2,3,5,11a-tetrahydro-1H benzo[e]pyrrolo[1,2-a][1,4]diazepi-5-one (5a);

(11aS)-7-(methyloxy)-8-(4-[(2-(methyloxy)-4-5-[3,4,5-tri(methyloxy)phenyl]-4,5-dihydro-3-isoxazolylphenyl)

oxy]butyloxy)-2,3,5,11a-tetrahydro-1H benzo[e]pyrrolo[1,2-a][1,4]diazepin-5-one (5b);

(11aS)-7-(methyloxy)-8-(5-[(2-(methyloxy)-4-5-[3,4,5-tri(methyloxy)phenyl]-4,5-dihydro-3-isoxazolylphenyl)oxy]pentyloxy)-2,3,5,11a-tetrahydro-1H benzo[e]pyrrolo[1,2-a][1,4]diazepi-5-one (5c);

(11aS)-7-(methyloxy)-8-(6-[(2-(methyloxy)-4-5-[3,4,5-tri(methyloxy)phenyl]-4,5-dihydro-3-isoxazolylphenyl)oxy]hexyloxy)-2,3,5,11a-tetrahydro-1H benzo[e]pyrrolo[1,2-a][1,4]diazepi-5-one (5d);

(11aS)-7-(methyloxy)-8-(3-[(2-(methyloxy)-5-3-[2,3,4-tri(methyloxy)phenyl]-4,5-dihydro-5-isoxazolylphenyl)oxy]propyloxy)-2,3,5,11a-tetrahydro-1H-benzo[e]pyrrolo[1,2-a][1,4]diazepin-5-one (9a);

(11aS)-7-(methyloxy)-8-(4-[(2-(methyloxy)-5-3-[2,3,4-tri(methyloxy)phenyl]-4,5-dihydro-5-isoxazolylphenyl)oxy]butyloxy)-2,3,5,11a-tetrahydro-1H-benzo[e]pyrrolo[1,2-a][1,4]diazepin-5-one (9b);

(11aS)-7-(methyloxy)-8-(5-[(2-(methyloxy)-5-3-[2,3,4-tri(methyloxy)phenyl]-4,5-dihydro-5-isoxazolylphenyl)oxy]pentyloxy)-2,3,5,11a-tetrahydro-1H-benzo[e]pyrrolo[1,2-a][1,4]diazepin-5-one (9c);

(11aS)-7-(methyloxy)-8-(6-[(2-(methyloxy)-5-3-[2,3,4-tri(methyloxy)phenyl]-4,5-dihydro-5-isoxazolylphenyl)oxy]hexyloxy)-2,3,5,11a-tetrahydro-1H-benzo[e]pyrrolo[1,2-a][1,4]diazepin-5-one (9d);

(11aS)-8-(3-[(2,6-di(methyloxy)-4-3-[2,3,4-tri(methyloxy)phenyl]-4,5-dihydro-5-isoxazolylphenyl)oxy]propyloxy)-7-(methyloxy)-2,3,5,11a-tetrahydro-1H-benzo[e]pyrrolo[1,2-a][1,4]diazepin-5-one (9e);

(11aS)-8-(4-[(2,6-di(methyloxy)-4-3-[2,3,4-tri(methyloxy)phenyl]-4,5-dihydro-5-isoxazolylphenyl)oxy]butyloxy)-7-(methyloxy)-2,3,5,11a-tetrahydro-1H-benzo[e]pyrrolo[1,2-a][1,4]diazepin-5-one (9f);

(11aS)-8-(5-[(2,6-di(methyloxy)-4-3-[2,3,4-tri(methyloxy)phenyl]-4,5-dihydro-5-isoxazolylphenyl)oxy]pentyloxy)-7-(methyloxy)-2,3,5,11a-tetrahydro-1H-benzo[e]pyrrolo[1,2-a][1,4]diazepin-5-one (9g);

(11aS)-8-(6-[(2,6-di(methyloxy)-4-3-[2,3,4-tri(methyloxy)phenyl]-4,5-dihydro-5-isoxazolylphenyl)oxy]hexyloxy)-7-(methyloxy)-2,3,5,11a-tetrahydro-1H-benzo[e]pyrrolo[1,2-a][1,4]diazepin-5-one (9h);

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and Synthesis of new congeners as illustrated in Scheme-1, which comprise:
1. The ether linkage at C-8 position of DC-81 intermediates with isoxazolines.
2. Refluxing the reaction mixtures for 48 h.
3. Synthesis of C-8 linked PBD antitumour antibiotic hybrid imines.
4. Purification by column chromatography using different solvents like ethyl acetate, hexane, dichloromethane and methanol.

Scheme 1

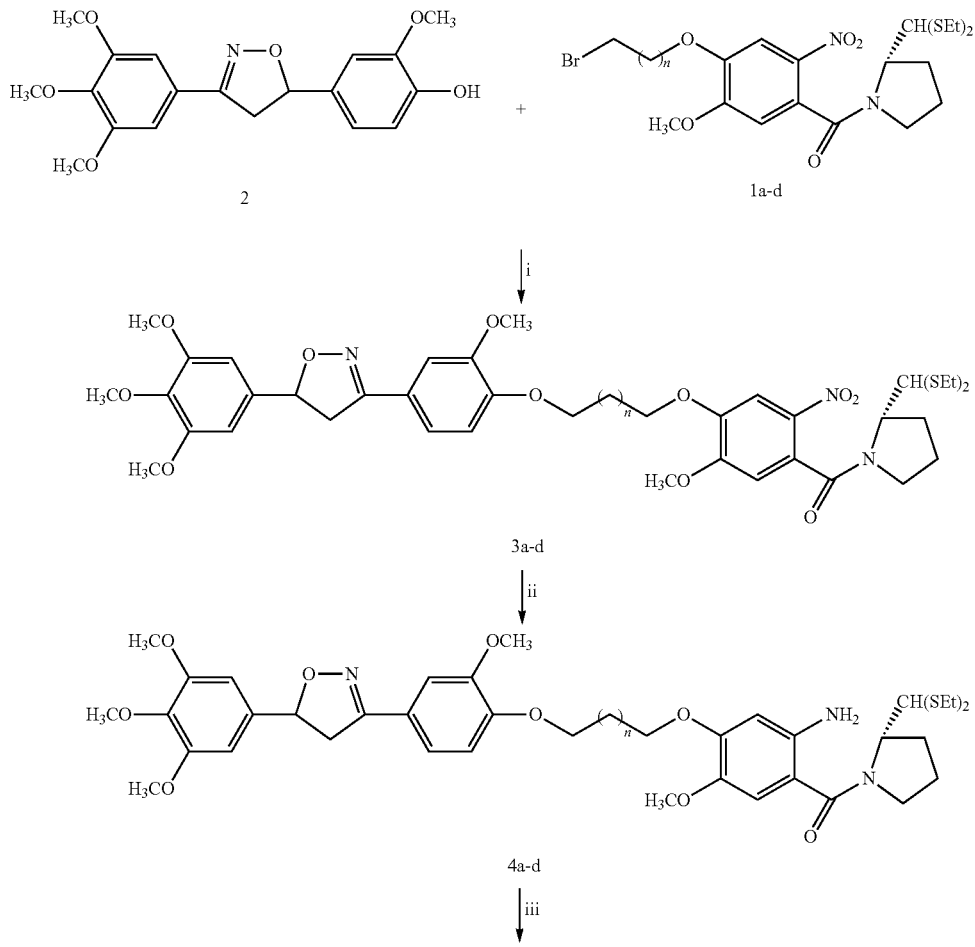

-continued
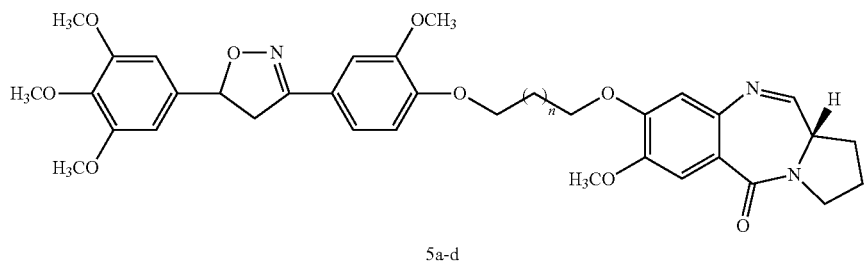
5a-d
$n = 1, 2, 3, 4$
Reagents and conditions: (i) $K_2CO_3$, acetone, 18 h, reflux, 90-92%; (ii) $SnCl_2 \cdot 2H_2O$, MeOH, 2 h, reflux, 85-87%; (iii) $HgCl_2$—$CaCO_3$, $CH_3CN$—$H_2O$ (4:1), 12 h, rt, 68-71%.
Scheme 2
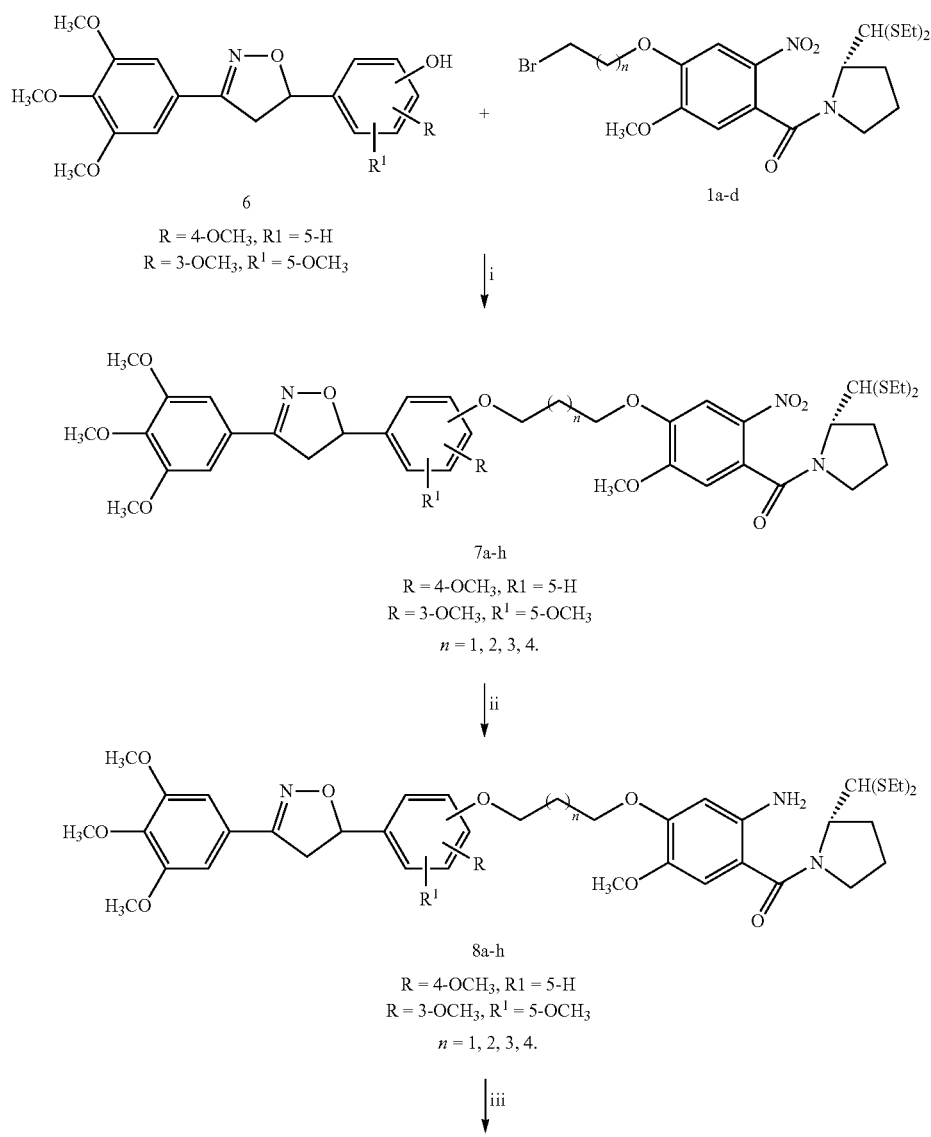

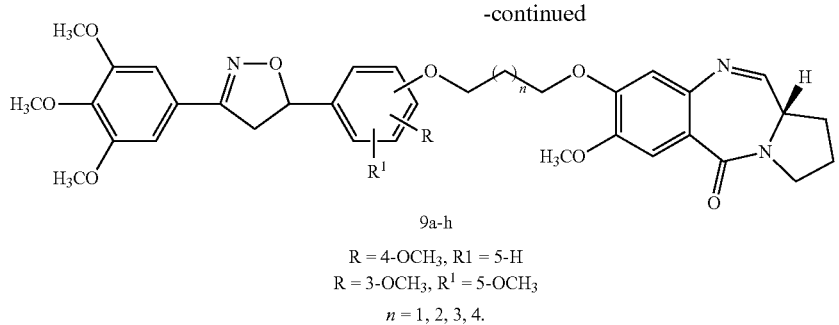

9a-h

R = 4-OCH₃, R¹ = 5-H
R = 3-OCH₃, R¹ = 5-OCH₃ n = 1, 2, 3, 4.

Reagents and conditions: (i) K₂CO₃, acetone, 18 h, reflux, 90-92%; (ii) SnCl₂•2H₂O, MeOH, 2 h, reflux, 85-87%; (iii) HgCl₂—CaCO₃, CH₃CN—H₂O (4:1), 12 h, rt, 68-71%.

The following examples are given by way of illustration and therefore should not be construed to the present limit of the scope of invention.

Example-1

2S-2-[di(ethylsulfanyl)methyl]tetrahydro-1H-1-pyr-rolyl[5-methoxy-4-(3-2-methoxy-4-[5-(3,4,5-tri-methoxyphenyl)-4,5-dihydro-3-isoxazolyl]phenox-ypropoxy)-2-nitrophenyl]methanone (3a)

To a solution of 2S—N-[4-(3-bromopropoxy)-5-methoxy-2-nitrobenzoyl]pyrrolidine-2-carboxaldehyde diethylthioac-etal (1a) (521 mg, 1.0 mmol) in dry acetone (20 mL) was added anhydrous potassium carbonate (690 mg, 5.0 mmol) and 4-(4,5-dihydro-5-(3,4,5-trimethoxyphenyl)isoxazol-3-yl)-2-methoxyphenol of formula (2) (359 mg, 1.0 mmol). The reaction mixture was refluxed in an oil bath for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hex-ane (6:4) as a solvent system to obtain the pure product (3a) (639 mg, 80% yield).

¹H NMR (CDCl₃): δ 1.23-1.39 (m, 8H), 1.78-2.33 (m, 4H), 2.72-2.86 (m, 4H), 3.21-3.29 (m, 2H), 3.30-3.38 (dd, 1H, J=8.7, J=16.4 Hz), 3.69-3.82 (dd, 1H, J=10.7, J=16.4 Hz), 3.84 (s, 3H), 3.87 (s, 6H), 3.89 (s, 3H), 3.92 (s, 3H), 4.25-4.45 (t, 4H, J=6.79 Hz), 4.68-4.74 (m, 1H), 4.88 (d, 1H, J=3.7 Hz), 5.63-5.70 (dd, 1H, J=8.6, J=10.7 Hz), 6.81 (s, 1H), 6.85 (s, 1H), 6.87 (d, 1H, J=8.3 Hz), 7.05 (d, 1H, J=8.3 Hz), 7.40-7.42 (m, 1H), 7.69 (s, 1H); MS (ESI): m/z 800 (M+1)⁺.

2-amino-5-methoxy-4-(3-2-methoxy-4-[5-(3,4,5-trimethoxyphenyl)-4,5-dihydro-3-isox-azolyl]phe-noxypropoxy)phenyl]-2S)-2-[di(ethylsulfanyl)me-thyl]tetrahydro-1H-1-pyrrol-ylmethanone (4a)

2 S-2-[di(ethylsulfanyl)methyl]tetrahydro-1H-1-pyrrolyl [5-methoxy-4-(3-2-methoxy-4-[5-(3,4,5-trimethoxyphe-nyl)-4,5-dihydro-3-isoxazolyl]phenoxypropoxy)-2-nitro-phenyl]methanone (3a) (799 mg, 1.0 mmol) was dissolved in methanol (10 mL), SnCl₂.2H₂O (1.12 g, 5.0 mmol) was added and refluxed until the TLC indicated the completion of the reaction. The methanol was then evaporated in vacuum and the aqueous layer was then adjusted to pH 8 with 10% NaHCO₃ solution and extracted with ethyl acetate (60 mL). The combined organic phase was dried over Na₂SO₄ and evaporated under vacuum to afford the crude amino dieth-ylthioacetal 4a (746 mg, 97% yield), which was directly used in the next step.

(11aS)-7-(methyloxy)-8-(3-[(2-(methyloxy)-4-5-[3,4,5-tri(methyloxy)phenyl]-4-,5-dihyd-ro-3-isoxado-lylphenyl)oxy]propyloxy)-2,3,5,11a-tetrahydro-1H benzo[e]pyrrolo[1,2-a][1,4]diazepi-5-one. (5a)

A solution of 2-amino-5-methoxy-4-(3-2-methoxy-4-[5-(3,4,5-trimethoxyphenyl)-4,5-dihydro-3-isoxazolyl]phenox-ypropoxy)phenyl](2S)-2-[di(ethylsulfanyl)methyl]tetrahyd-ro-1H-1-pyrrolylmethanone (4a) (769 mg, 1.0 mmol), HgCl₂ (576 mg, 2.26 mmol) and CaCO₃ (225 mg, 2.46 mmol) in acetonitrile-water (4:1) was stirred slowly at room temperature overnight until complete consumption of starting material as indicated by the TLC. The clear organic supernatant liquid was extracted with ethyl acetate and washed with saturated 5% NaHCO₃ (20 mL), brine (20 mL) and the combined organic phase was dried over Na₂SO₄. The organic layer was evaporated in vacuo to afford a white solid, which was first eluted on a column chromatography with ethyl acetate to remove mercuric salts, and then with ethyl acetate to obtain the pure product 5a (374 mg, 58% yield).

¹H NMR (CDCl₃): δ 0.81-0.92 (m, 2H), 1.25-1.75 (m, 2H), 1.98-2.39 (m, 2H), 3.26-3.39 (dd, 1H, J=8.7, J=16.4 Hz), 3.52-3.62 (dd, 1H, J=10.7, J=16.4 Hz), 3.68-3.76 (m, 3H), 3.83 (s, 3H), 3.87 (s, 6H), 3.90 (s, 3H), 4.25-4.45 (t, 4H, J=6.7 Hz), 5.61-5.72 (dd, 1H, J=8.6, J=10.7 Hz), 6.61 (s, 2H), 6.83 (s, 1H), 6.87 (d, 1H, J=8.6 Hz), 7.05 (d, 1H, J=8.6 Hz), 7.42 (s, 1H), 7.51 (s, 1H), 7.68 (d, 1H, J=4.3 Hz); MS (ESI): m/z 646 (M+1)⁺.

Example-2

2S-2-[di(ethylsulfanyl)methyl]tetrahydro-1H-1-pyr-rolyl[5-methoxy-4-(4-2-methoxy-4-[5-(3,4,5-tri-methoxyphenyl)-4,5-dihydro-3-isoxazolyl]phenoxy-butoxy)-2-nitrophenyl]methanone (3b)

This compound was prepared according to the method described for the compound 3a by employing 2S—N-[4-(4-bromobutoxy)-5-methoxy-2-nitrobenzoyl]pyrrolidine-2-carboxaldehyde (1b) diethylthioacetal (535 mg, 1.0 mmol) was added anhydrous potassium carbonate (690 mg, 5.0 mmol) and 4-(4,5-dihydro-5-(3,4,5-trimethoxyphenyl)isox-azol-3-yl)-2-methoxyphenol of formula (2) (359 mg, 1.0 mmol) to obtain the pure product 3b (683 mg, 84% yield).

¹H NMR (CDCl₃): δ1.23-1.39 (m, 10H), 1.78-2.33 (m, 4H), 2.72-2.86 (m, 4H), 3.21-3.29 (m, 2H), 3.30-3.38 (dd, 1H, J=8.7, J=16.4 Hz), 3.69-3.82 (dd, 1H, J=10.7, J=16.4 Hz), 3.84 (s, 3H), 3.87 (s, 6H), 3.89 (s, 3H), 3.92 (s, 3H), 4.11-4.18 (m, 4H), 4.68-4.74 (m, 1H), 4.88 (d, 1H, J=3.7 Hz), 5.63-5.70 (dd, 1H, J=8.6, J=10.7 Hz), 6.81 (s, 1H), 6.85 (s, 1H), 6.87 (d, 1H, J=8.3 Hz), 7.05 (d, 1H, J=8.3 Hz), 7.40-7.42 (m, 1H), 7.69 (s, 1H); MS (ESI): m/z 814 (M+1)⁺.

2-amino-5-methoxy-4-(4-2-methoxy-4-[5-(3,4,5-trimethoxyphenyl)-4,5-dihydro-3-isoxazolyl]phenoxybutoxy)phenyl](2S)-2-[di(ethylsulfanyl)methyl]tetrahydro-1H-1-pyrrolylmethanone (4b)

This compound was prepared according to the method described for the compound 4a by reducing 2S-2-[di(ethylsulfanyl)methyl]tetrahydro-1H-1-pyrrolyl[5-methoxy-4-(4-2-methoxy-4-[5-(3,4,5-trimethoxyphenyl)-4,5-dihydro-3-isoxazolyl]phenoxybutoxy)-2-nitrophenyl]methanone (3b) (813 mg, 1.0 mmol) using $SnCl_2.2H_2O$ (1.12 g, 5.0 mmol). The amino compound 4b obtained was (759 mg, 97% yield).

(11aS)-7-(methyloxy)-8-(4-[(2-(methyloxy)-4-5-[3,4,5-tri(methyloxy)phenyl]-4,5-dihydro-3-isoxazolylphenyl)oxy]butyloxy)-2,3,5,11a-tetrahydro-1H-benzo[e]pyrrolo[1,2-a][1,4]diazepin-5-one. (5b)

This compound was prepared according to the method described for the compound 5a 2-amino-5-methoxy-4-(4-2-methoxy-4-[5-(3,4,5-trimethoxyphenyl)-4,5-dihydro-3-isoxazolyl]phenoxybutoxy)phenyl]-2S)-2-[di(ethylsulfanyl)methyl]tetrahydro-1H-1-pyrrolylmethanone (4b) (783 mg, 1.0 mmol) and $HgCl_2$ (582 mg, 2.26 mmol), $CaCO_3$ (230 mg, 2.46 mmol) in acetonitrile-water (4:1) to obtain the pure product 5b (382 mg, 58% yield).).

$^1H$ NMR ($CDCl_3$): δ 0.81-0.92 (m, 4H), 1.25-1.75 (m, 2H), 1.98-2.39 (m, 2H), 3.26-3.39 (dd, 1H, J=8.7, J=16.4 Hz), 3.52-3.62 (dd, 1H, J=10.7, J=16.4 Hz), 3.68-3.76 (m, 3H), 3.83 (s, 3H), 3.87 (s, 6H), 3.90 (s, 3H), 4.11-4.18 (m, 4H), 5.61-5.72 (dd, 1H, J=8.6, J=10.7 Hz), 6.61 (s, 2H), 6.83 (s, 1H), 6.87 (d, 1H, J=8.6 Hz), 7.05 (d, 1H, J=8.6 Hz), 7.42 (s, 1H), 7.51 (s, 1H), 7.68 (d, 1H, J=4.3 Hz); MS (ESI): m/z 660 $(M+1)^+$.

Example-3

2S-2-[di(ethylsulfanyl)methyl]tetrahydro-1H-1-pyrrolyl[5-methoxy-4-(4-2-methoxy-4-[5-(3,4,5-trimethoxyphenyl)-4,5-dihydro-3-isoxazolyl]phenoxypentyl)oxy)-2-nitrophen-yl]methanone (3c)

This compound was prepared according to the method described for the compound 3a by employing 2S—N-[4-(5-bromophenyloxy)-5-methoxy-2-nitrobenzoyl]pyrrolidine-2-carboxaldehyde diethylthioacetal (1c) (549 mg, 1.0 mmol) was added anhydrous potassium carbonate (690 mg, 5.0 mmol) and 4-(4,5-dihydro-5-(3,4,5-trimethoxyphenyl)isoxazol-3-yl)-2-methoxyphenol of formula (2) (359 mg, 1.0 mmol) to obtain the pure product 3c (719 mg, 87% yield).

$^1H$ NMR ($CDCl_3$): δ1.23-1.39 (m, 12H), 1.78-2.33 (m, 4H), 2.72-2.86 (m, 4H), 3.21-3.29 (m, 2H), 3.30-3.38 (dd, 1H, J=8.7, J=16.4 Hz), 3.69-3.82 (dd, 1H, J=10.7, J=16.4 Hz), 3.84 (s, 3H), 3.87 (s, 6H), 3.89 (s, 3H), 3.92 (s, 3H), 4.25-4.45 (t, 4H, J=6.79 Hz), 4.68-4.74 (m, 1H), 4.88 (d, 1H, J=3.7 Hz), 5.63-5.70 (dd, 1H, J=8.6, J=10.7 Hz), 6.81 (s, 1H), 6.85 (s, 1H), 6.87 (d, 1H, J=8.3 Hz), 7.05 (d, 1H, J=8.3 Hz), 7.40-7.42 (m, 1H), 7.69 (s, 1H); MS (ESI): m/z 828 $(M+1)^+$.

2-amino-5-methoxy-4-[(5-2-methoxy-4-[5-(3,4,5-trimethoxyphenyl)-4,5-dihydro-3-iso-oxazolyl]phenoxypentyl)oxy]phenyl(2S)-2-[di(ethylsulfanyl)methyl]tetrahydro-1H-1-pyrrolylmethanone (4c)

This compound was prepared according to the method described for the compound 4a by reducing a solution of 2S-2-[di(ethylsulfanyl)methyl]tetrahydro-1H-1-pyrrolyl[5-methoxy-4-(4-2-methoxy-4-[5-(3,4,5-trimethoxyphenyl)-4,5-dihydro-3-isoxazolyl]phen-oxypentyl)oxy)-2-nitrophenyl]methanone (3c) (827 mg, 1.0 mmol) using $SnCl_2.2H_2O$ (1.12 g, 5.0 mmol). The amino compound 4c obtained was (773 mg, 97% yield).

(11aS)-7-(methyloxy)-8-(5-[(2-(methyloxy)-4-5-[3,4,5-tri(methyloxy)phenyl]-4,5-dihyd-ro-3-isoxazolylphenyl)oxy]pentyloxy)-2,3,5,11a-tetrahydro-1H benzo[e]pyrrolo[1,2-a][1,4]diazepi-5-one. (5c)

This compound was prepared according to the method described for the compound 5a empoying 2-amino-5-methoxy-4-[(5-2-methoxy-4-[5-(3,4,5-trimethoxyphenyl)-4,5-dihydro-3-isoxazolyl]phenoxypentyl)oxy]phenyl(2S)-2-[di(ethylsulfanyl)methyl]tetrahydro-1H-1-pyrrolylmethanone (4c) (797 mg, 1.0 mmol) and $HgCl_2$ (590 mg, 2.26 mmol), $CaCO_3$ (244 mg, 2.46 mmol) in acetonitrile-water (4:1) to obtain the pure product 5c (390 mg, 58% yield).

$^1H$ NMR ($CDCl_3$): δ 0.81-0.92 (m, 4H), 1.25-1.75 (m, 4H), 1.98-2.39 (m, 2H), 3.26-3.39 (dd, 1H, J=8.7, J=16.4 Hz), 3.52-3.62 (dd, 1H, J=10.7, J=16.4 Hz), 3.68-3.76 (m, 3H), 3.83 (s, 3H), 3.87 (s, 6H), 3.90 (s, 3H), 4.25-4.45 (t, 4H, J=6.7 Hz), 5.61-5.72 (dd, 1H, J=8.6, J=10.7 Hz), 6.61 (s, 2H), 6.83 (s, 1H), 6.87 (d, 1H, J=8.6 Hz), 7.05 (d, 1H, J=8.6 Hz), 7.42 (s, 1H), 7.51 (s, 1H), 7.68 (d, 1H, J=4.3 Hz); MS (ESI): m/z 674 $(M+1)^+$.

Example-4

(2S)-2-[di(ethylsulfanyl)methyl]tetrahydro-1H-1-pyrrolyl[5-methoxy-4-(3-2-methoxy-5-[3-(3,4,5-trimethoxyphenyl)-4,5-dihydro-5-isoxazolyl]phenoxypropoxy)-2-nitrophenyl]methanone (7a)

To a solution of 2S—N-[4-(3-bromopropoxy)-5-methoxy-2-nitrobenzoyl]pyrrolidine-2-carboxaldehyde diethylthioacetal (1a) (521 mg, 1.0 mmol) in dry acetone (20 mL) was added anhydrous potassium carbonate (690 mg, 5.0 mmol) and 3-hydroxy substituted isoxazoline of formula (6) (359 mg, 1.0 mmol). The reaction mixture was refluxed in an oil bath for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product (7a) (639 mg, 80% yield).

$^1H$ NMR ($CDCl_3$): δ 1.23-1.39 (m, 8H), 1.78-2.33 (m, 4H), 2.72-2.86 (m, 4H), 3.21-3.29 (m, 2H), 3.30-3.38 (dd, 1H, J=8.7, J=16.4 Hz), 3.69-3.82 (dd, 1H, J=10.7, J=16.4 Hz), 3.84 (s, 3H), 3.87 (s, 6H), 3.89 (s, 3H), 3.92 (s, 3H), 4.25-4.45 (t, 4H, J=6.79 Hz), 4.68-4.74 (m, 1H), 4.88 (d, 1H, J=3.7 Hz), 5.63-5.70 (dd, 1H, J=8.6, J=10.7 Hz), 6.81 (s, 1H), 6.85 (s, 1H), 6.87 (d, 1H, J=8.3 Hz), 7.05 (d, 1H, J=8.3 Hz), 7.40-7.42 (m, 1H), 7.69 (s, 1H); MS (ESI): m/z 800 $(M+1)^+$.

2-amino-5-methoxy-4-(3-2-methoxy-5-[3-(3,4,5-trimethoxyphenyl)-4,5-dihydro-5-isoxazolyl]phenoxypropoxy)phenyl](2S)-2-[di(ethylsulfanyl)methyl]tetrahydro-1H-1-pyrrolylmethanone (8a)

(2S)-2-[di(ethylsulfanyl)methyl]tetrahydro-1H-1-pyrrolyl[5-methoxy-4-(3-2-methoxy-5-[3-(3,4,5-trimethoxyphenyl)-4,5-dihydro-5-isoxazolyl]phenoxypropoxy)-2-nitrophenyl]methanone (7a) (799 mg, 1.0 mmol) was dissolved in methanol (10 mL), $SnCl_2.2H_2O$ (1.12 g, 5.0 mmol) was added and refluxed until the TLC indicated the completion of the reaction. The methanol was then evaporated in vacuum and the aqueous layer was then adjusted to pH 8 with 10% $NaHCO_3$ solution and extracted with ethyl acetate (60 mL). The combined organic phase was dried over $Na_2SO_4$ and evaporated under vacuum to afford the crude amino diethylthioacetal 8a (746 mg, 97% yield), which was directly used in the next step.

(11a S)-7-(methyloxy)-8-(3-[(2-(methyloxy)-5-3-[2, 3,4-tri(methyloxy)phenyl]-4,5-dihydro-5-isoxazolylphenyl)oxy]propyloxy)-2,3,5,11a-tetrahydro-1H-benzo[e]pyrrolo[1,2-a][1,4]diazepin-5-one. (9a)

A solution of 2-amino-5-methoxy-4-(3-2-methoxy-5-[3-(3, 4,5-trimethoxyphenyl)-4,5-dihydro-5-isoxazolyl]phenoxyepropoxy)phenyl](2S)-2-[di(ethylsulfanyl)methyl]tetrahydro-1H-1-pyrrolylmethanone (8a) (769 mg, 1.0 mmol), $HgCl_2$ (576 mg, 2.26 mmol) and $CaCO_3$ (225 mg, 2.46 mmol) in acetonitrile-water (4:1) was stirred slowly at room temperature overnight until complete consumption of starting material as indicated by the TLC. The clear organic supernatant liquid was extracted with ethyl acetate and washed with saturated 5% $NaHCO_3$ (20 mL), brine (20 mL) and the combined organic phase was dried over $Na_2SO_4$. The organic layer was evaporated in vacuo to afford a white solid, which was first eluted on a column chromatography with ethyl acetate to remove mercuric salts, and then with ethyl acetate to obtain the pure product 9a (374 mg, 58% yield).
$^1$H NMR ($CDCl_3$): δ 0.81-0.92 (m, 2H), 51.25-1.75 (m, 2H), 1.98-2.39 (m, 2H), 3.26-3.39 (dd, 1H, J=8.7, J=16.4 Hz), 3.52-3.62 (dd, 1H, J=10.7, J=16.4 Hz), 3.68-3.76 (m, 3H), 3.83 (s, 3H), 3.87 (s, 6H), 3.90 (s, 3H), 4.25-4.45 (t, 4H, J=6.7 Hz), 5.61-5.72 (dd, 1H, J=8.6, J=10.7 Hz), 6.61 (s, 2H), 6.83 (s, 1H), 6.87 (d, 1H, J=8.6 Hz), 7.05 (d, 1H, J=8.6 Hz), 7.42 (s, 1H), 7.51 (s, 1H), 7.68 (d, 1H, J=4.3 Hz); MS (ESI): m/z 646 (M+1)$^+$.

Example-5

(2S)-2-[(di(ethylsulfanyl)methyl]tetrahydro-1H-1-pyrrolyl[4-(3-2,6-dimethoxy-4-[3-(3,4,5-trimethoxyphenyl)-4,5-dihydro-5-isoxazolyl]phenoxypropoxy)-5-methoxy-2-nitrophenyl]methanone (7e)

To a solution of 2S—N-[4-(3-bromopropoxy)-5-methoxy-2-nitrobenzoyl]pyrrolidine-2-carboxaldehyde diethylthioacetal (1a) (521 mg, 1.0 mmol) in dry acetone (20 mL) was added anhydrous potassium carbonate (690 mg, 5.0 mmol) and 4-hydroxy substituted isoxazoline of formula (6) (389 mg, 1.0 mmol). The reaction mixture was refluxed in an oil bath for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product (7e) (676 mg, 80% yield).
$^1$H NMR ($CDCl_3$): δ 1.23-1.39 (m, 8H), 1.78-2.33 (m, 4H), 2.72-2.86 (m, 4H), 3.21-3.29 (m, 2H), 3.30-3.38 (dd, 1H, J=8.7, J=16.4 Hz), 3.69-3.82 (dd, 1H, J=10.7, J=16.4 Hz), 3.84 (s, 3H), 3.87 (s, 6H), 3.89 (s, 3H), 3.92 (s, 3H), 4.25-4.45 (t, 4H, J=6.79 Hz), 4.68-4.74 (m, 1H), 4.88 (d, 1H, J=3.7 Hz), 5.63-5.70 (dd, 1H, J=8.6, J=10.7 Hz), 6.55 (s, 2H), 6.74 (s, 1H), 6.92 (s, 2H), 7.69 (s, 1H); MS (ESI): m/z 846 (M+1)$^+$.

2-amino-4-(3-2,6-dimethoxy-4-[3-(3,4,5-trimethoxyphenyl)-4,5-dihydro-5-isoxazolyl]phenoxypropoxy)-5-methoxyphenyl)-2S)-2-[di(ethylsulfanyl) methyl]tetrahydro-1H-1-pyrrolylmethanone. (8e)

(2S)-2-[di(ethylsulfanyl)methyl]tetrahydro-1H-1-pyrrolyl[4-(3-2,6-dimethoxy-4-[3-(3,4,5-trimethoxyphenyl)-4,5-dihydro-5-isoxazolyl]phenoxypropoxy)-5-methoxy-2-nitrophenyl]methanone (7e) (845 mg, 1.0 mmol) was dissolved in methanol (10 mL), $SnCl_2.2H_2O$ (1.12 g, 5.0 mmol) was added and refluxed until the TLC indicated the completion of the reaction. The methanol was then evaporated in vacuum and the aqueous layer was then adjusted to pH 8 with 10% $NaHCO_3$ solution and extracted with ethyl acetate (60 mL). The combined organic phase was dried over $Na_2SO_4$ and evaporated under vacuum to afford the crude amino diethylthioacetal 8e (791 mg, 97% yield), which was directly used in the next step.

(11aS)-8-(3-2,6-dimethoxy-4-[3-(3,4,5-trimethoxyphenyl)-4,5-dihydro-5-isoxazolyl]phenoxypropoxy)-7-methoxy-2,3,5,11a-tetrahydro-1H-benzo[e]pyrrolo[1,2-a][1,4]diazepin-5-one. (9e)

A solution of 2-amino-4-(3-2,6-dimethoxy-4-[3-(3,4,5-trimethoxyphenyl)-4,5-dihydro-5-isoxazolyl]phenoxypropoxy)-5-methoxyphenyl](2S)-2-[di(ethylsulfanyl)methyl]tetrahydro-1H-1-pyrrolylmethanone (8e) (815 mg, 1.0 mmol), $HgCl_2$ (576 mg, 2.26 mmol) and $CaCO_3$ (225 mg, 2.46 mmol) in acetonitrile-water (4:1) was stirred slowly at room temperature overnight until complete consumption of starting material as indicated by the TLC. The clear organic supernatant liquid was extracted with ethyl acetate and washed with saturated 5% $NaHCO_3$ (20 mL), brine (20 mL) and the combined organic phase was dried over $Na_2SO_4$. The organic layer was evaporated in vacuo to afford a white solid, which was first eluted on a column chromatography with ethyl acetate to remove mercuric salts, and then with ethyl acetate to obtain the pure product 9e (392 mg, 58% yield).
$^1$H NMR ($CDCl_3$): δ 0.81-0.92 (m, 2H), 1.25-1.75 (m, 2H), 1.98-2.39 (m, 2H), 3.26-3.39 (dd, 1H, J=8.7, J=16.4 Hz), 3.52-3.62 (dd, 1H, J=10.7, J=16.4 Hz), 3.68-3.76 (m, 3H), 3.83 (s, 3H), 3.87 (s, 6H), 3.90 (s, 3H), 4.25-4.45 (t, 4H, J=6.7 Hz), 5.61-5.72 (dd, 1H, J=8.6, J=10.7 Hz), 6.55 (s, 2H), 6.83 (s, 1H), 7.05 (s, 2H), 7.51 (s, 1H), 7.68 (d, 1H, J=4.3 Hz); MS (ESI): m/z 676 (M+1)$^+$.

Biological Activity: The in vitro biological activity studies were carried out at the National Cancer Institute, Maryland, USA.
Cytotoxicity:
the compounds (11aS)-7-(methyloxy)-8-(4-[(2-(methyloxy)-4-5-[3,4,5-tri(methyloxy)-phenyl]-4,5-dihydro-3-isoxazolylphenyl)oxy]butyloxy)-2,3,5,11a-tetrahydro-1H benzo[e]pyrrolo[1,2-a][1,4]diazepin-5-one (5b);
(11aS)-7-(methyloxy)-8-(4-[(2-(methyloxy)-5-3-[2,3,4-tri(methyloxy)phenyl]-4,5-dihydro-5-isoxazolylphenyl)oxy]butyloxy)-2,3,5,11a-tetrahydro-1H-benzo[e]pyrrolo[1,2-a][1,4]diazepin-5-one (9b);
Biological Activity of C8-Linked Isoxazoline-PBD Hybrids: In Vitro Cytotoxicity The C8-linked isoxazoline-PBD hybrids have been tested against sixty human tumour cell lines derived from nine cancer types (leukemia, non-small cell lung cancer, colon cancer, CNS cancer, melanoma, ovarian cancer, renal cancer, prostate cancer and breast cancer) as per NCI protocol. For each compound, dose response curves for individual cell lines have been measured at a minimum of five concentrations at 10 fold dilutions. A protocol of 48 hrs continuous drug exposure has been used, and a sulforhodamine B (SRB) protein assay was used to estimate cell viability or growth. The concentration for 50% cell growth inhibition ($GI_{50}$), total cell growth inhibition (TGI, 0% growth) and 50% cell death ($LC_{50}$, 50% growth) compared with the control has been calculated (FIG. 2).

Compound 5b and 9b have been evaluated for in vitro cytotoxicity in sixty cell lines from nine human cancer types of lung (Hop-62, NCI-H226, NCI-H522), leukemia (K-562, SR), colon (HCT-116, HCT-15, HCC-2998), CNS(SF-539), melanoma (SK-MEL-5, UACC-62, M14), ovarian (IGROV1), renal (A498), prostate (PC3) breast (BT-549, MDA-MB-435, HS578T) origin. The results are expressed as percent of cell growth determined relative to that of untreated control cells (Table 1). The representative compound 5b has shown significant cytotoxicity against some cancer cell lines.

TABLE 1

$Log_{10}$ GI50 (concentration in mol/L) and $Log_{10}$ LC50 (concentration in mol/L causing 50% lethality) values for the representative compound 5b

| Cancer | $Log_{10}$GI50 | | $Log_{10}$LC50 | |
|---|---|---|---|---|
| | 5b | 9b | 5b | 9b |
| Leukemia | −6.76 | −5.83 | −4.18 | −4.37 |
| Non small cell lung cancer | −6.59 | −5.70 | −4.78 | −4.73 |
| CNS | −6.51 | −5.74 | −5.18 | −5.05 |
| Melanoma | −6.68 | −5.72 | −5.82 | −5.12 |
| Ovarian | −6.44 | −5.61 | −4.84 | −4.48 |
| Renal | −6.58 | −5.62 | −4.94 | −4.77 |
| Prostate | −6.49 | −5.92 | −4.82 | −4.54 |
| Breast | −6.74 | −5.74 | −4.52 | −4.34 |

Each cancer type represents the average of six to eight different cancer cell lines.

The compound 5b exhibits a wide spectrum of activity against sixty cell lines in nine cell panels, with $GI_{50}$ value of <0.47 μm. In the non-small cell lung cancer panel, the growth of HOP-62, NCI-H226, NCI-H522 cell lines were affected by compound 5b with $GI_{50}$ values as 0.27, 0.31 and 0.12 μm respectively. The $GI_{50}$ values of compound 5b against colon cancer HCT-116, HCT-15 and HCC-2998 cell lines are 0.18, 0.19 and 0.19 μm respectively. The $GI_{50}$ values for compound 5b against leukemia K-562, and SR cell lines are 0.12, 0.14 μm respectively. The $GI_{50}$ values for compound 5b against CNS SF-539 cell line is 0.22 μm The $GI_{50}$ values for compound 5b against melanoma SK-MEL-5, UACC-62, and M14 cell lines are 0.20, 0.16, and 0.18 μm respectively. The $GI_{50}$ values for compound 5b against ovarian IGROV1 cell line is 0.24 μm The $GI_{50}$ values for compound 5b against renal A498 cell line is 0.18 μM. The $GI_{50}$ value for compound 5b against prostate PC-3 cell line is 0.32 μm The $GI_{50}$ values for compound 5b against breast BT-549, MDA-MB-435, and HS 578T cell lines are 0.09, 0.17, and 0.16 μm respectively.

Compounds 5b and 9b exhibit activity against sixty cell lines in nine cancer cell panels with $GI_{50}$ values of <0.47 and 3.54 μM respectively. Compare 5b and 9b, the compound 5b ten folds higher activity than 9b, in vitro cytotoxicity of compounds 5b and 9b in selected cancer cell lines have been illustrated in Table 2. The average $GI_{50}$ values for each cancer panel of compounds 5b and 9b have been illustrated in Table 2.

TABLE 2

In vitro cytotoxicity of compounds 5b and 9b in selected cancer cell lines

| Cancer panel/cell line | $GI_{50}$ (μM) | | Cancer panel/cell line | $GI_{50}$ (μM) | |
|---|---|---|---|---|---|
| | 5b | 9b | | 5b | 9b |
| Leukemia | | | Ovarian | | |
| CCRF-CEM | 0.16 | 1.41 | IGROV1 | 0.24 | 1.57 |
| HL-60(TB) | 0.18 | 1.90 | OVCAR-3 | 0.27 | 1.94 |
| K-562 | 0.12 | 1.26 | OVCAR-4 | 0.40 | 2.07 |
| MOLT-4 | 0.20 | 1.85 | OVCAR-5 | 0.42 | 3.13 |
| RPMI-8226 | 0.24 | 1.43 | OVCAR-8 | 0.37 | 2.55 |
| SR | 0.14 | 1.12 | SK-OV-3 | 0.47 | 3.37 |
| Non-smallcell lung | | | Renal | | |
| A549/ATCC | 0.26 | 2.33 | 786-0 | 0.28 | 1.57 |
| EKVX | 0.46 | 3.68 | A498 | 0.18 | 1.72 |

TABLE 2-continued

In vitro cytotoxicity of compounds 5b and 9b in selected cancer cell lines

| Cancer panel/cell line | $GI_{50}$ (μM) | | Cancer panel/cell line | $GI_{50}$ (μM) | |
|---|---|---|---|---|---|
| | 5b | 9b | | 5b | 9b |
| HOP-62 | 0.27 | 1.68 | ACHN | 0.28 | 2.41 |
| HOP-92 | 0.31 | 2.47 | CAKI-1 | 0.25 | 3.09 |
| NCI-H226 | 0.17 | 1.67 | RXF 393 | 0.21 | 1.39 |
| NCI-H23 | 0.27 | 1.83 | SN12C | 0.30 | 1.58 |
| NCI-H322M | 0.34 | 3.46 | TK-10 | 0.28 | 3.51 |
| NCI-H460 | 0.21 | 1.85 | UO-31 | 0.29 | 2.09 |
| NCI-H522 | 0.12 | 0.61 | | | |
| Colon | | | Breast | | |
| COLO 205 | 0.21 | 1.96 | MCF7 | 0.20 | 1.75 |
| HCC-2998 | 0.19 | 1.58 | MDA-MB- | 0.19 | 1.15 |
| HCT-116 | 0.18 | 1.70 | HS 578T | 0.16 | 1.10 |
| HCT-15 | 0.18 | 2.27 | MDA-MB-435 | 0.17 | 3.54 |
| HT29 | 0.36 | 2.75 | BT-549 | 0.09 | 1.23 |
| KM12 | 0.22 | 1.74 | T-47D | 0.28 | 1.31 |
| SW-620 | 0.23 | 1.55 | MDA-MB-468 | 0.22 | 1.34 |
| CNS | | | Prostate | | |
| SF-268 | 0.34 | 1.89 | PC-3 | 0.32 | 0.58 |
| SF-539 | 0.22 | 1.80 | DU-145 | 0.32 | 2.48 |
| SNB-19 | 0.34 | 1.96 | | | |
| SNB-75 | 0.32 | 1.71 | | | |
| U251 | 0.30 | 1.73 | | | |
| Melanoma | | | Melanoma | | |
| LOX IMVI | 0.22 | 1.47 | SK-MEL-28 | 0.20 | 2.07 |
| MALME-3M | 0.21 | 2.88 | SK-MEL-5 | 0.16 | 1.47 |
| M14 | 0.18 | 1.73 | UACC-257 | 0.27 | 2.33 |
| SK-MEL-2 | 0.23 | 2.03 | UACC-62 | 0.16 | 1.52 |

The mean graph mid point values of $log_{10}$ TGI and $log_{10}$ $LC_{50}$ as well as $log_{10}$ $GI_{50}$ for 5b and 9b are listed in Table-3. As demonstrated by mean graph pattern, compounds 5b and 9b exhibit an interesting profile of activity and selectivity for various cell lines. The mean graph mid points of $log_{10}$) TGI and $log_{10}$ $LC_{50}$ have shown similar pattern to the $log_{10}$ $GI_{50}$ mean graph mid points.

TABLE 3

$log_{10}$ $GI_{50}$, $log_{10}$ TGI and $log_{10}$ $LC_{50}$ mean graphs midpoints (MG_MID) of in vitro cytotoxicity data for the compound 5b against human tumour cell lines.

| Compound | $Log_{10}$ $GI_{50}$ | $Log_{10}$ TGI | $Log_{10}$ $LC_{50}$ |
|---|---|---|---|
| 5b | −6.59 | −6.05 | −4.98 |
| 9b | −5.73 | −5.28 | −4.72 |

DNA-Binding Ability of Novel C8-Linked Isoxazoline-PBD Hybrids
Thermal Denaturation Studies Compounds have been subjected to thermal denaturation studies with duplex-form calf thymus DNA (CT-DNA) using a modification of a reported procedure. Working solutions in aqueous buffer (10 mM $NaH_2PO_4$/$Na_2HPO_4$, 1 mM $Na_2EDTA$, pH 7.00+0.01) containing CT-DNA (100 (μm in phosphate) and the PBD (20(μm) have been prepared by addition of concentrated PBD solutions in DMSO to obtain a fixed [PBD]/[DNA] molar ratio of 1:5. The DNA-PBD solutions have been incubated at 37° C. for 0 and 18 hrs prior to analysis. Samples have been monitored at 260 nm using a Beckman DU-800 spectrophotometer fitted with high performance temperature controller, and heated at 1° C. $min^{-1}$ in the 40-110° C. range. DNA helix→coil transition temperatures ($T_m$) have been obtained from the maxima in the d($A_{260}$)/d T derivative plots. Drug-induced alterations in DNA melting behavior are given by: $\Delta T_m = T_m(DNA+PBD) - T_m(DNA$ alone), where the $T_m$ value for the PBD-free CT-DNA is 68.5±0.01. The fixed [PBD]/[DNA] ratio used has not resulted in binding saturation of the host DNA duplex for any compound examined.

The DNA-binding for these novel C8-linked isoxazoline-PBD hybrids has been examined by thermal denaturation studies using calf thymus CT-DNA. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. Interestingly, in this assay one of the isoxazoline-PBD hybrids (5c) elevates the helix melting temperature of CT-DNA by a margin of 8° C. after incubation for 18 h at 37° C. Data for 5a-c, 9b and 9g and DC-81 are included in Table 4 for comparison.

TABLE 4

Thermal denaturation data for isoxazoline-PBD hybrids with calf thymus CT-DNA

| PBD hybrids | [PBD]:[DNA] molar ratio[b] | $\Delta T_m$ (° C.)[a] after incubation at 37° C. for | |
|---|---|---|---|
| | | 0 hrs | 18 hrs |
| 5a | 1:5 | 3.9 | 6.0 |
| 5b | 1:5 | 4.1 | 6.2 |
| 5c | 1:5 | 7.0 | 8.0 |
| 9b | 1:5 | 1.2 | 2.3 |
| 9g | 1:5 | 1.4 | 2.1 |
| DC-81 | 1:5 | 0.3 | 0.7 |

[a] For CT-DNA alone at pH 7.00 ± 0.01, $T_m$ = 68.5° C. ± 0.01 (mean value from 10 separate determinations), all $\Delta T_m$ values are ± 0.1-0.2° C.
[b] For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].
[c] The $\Delta T_m$ for PBD hybrids 5a, 5b and 5c at a [PBD]:[DNA] molar ratio of 1:5 increased to a value of 6.0° C., 6.2° C. and 8.0° C. after 18 h incubation respectively.

Significance of the Work Carried Out

The novel C8-linked isoxazoline-PBD hybrids that have been synthesized exhibited significant DNA-binding ability and showed cytotoxic activity against sixty human tumour cell lines. Some of these hybrids exhibited promising DNA-binding activity. Among these hybrids the compound 5c show high DNA-binding ability (8° C.).

ADVANTAGES OF THE INVENTION

1. The present invention provides new pyrrolo[2,1-c][1,4]benzodiazepine hybrids useful as antitumour agents.
2. It also provides a process for the preparation of novel pyrrolo[2,1-c][1,4]benzodiazepine hybrids

We claim:
1. A compound of formula A

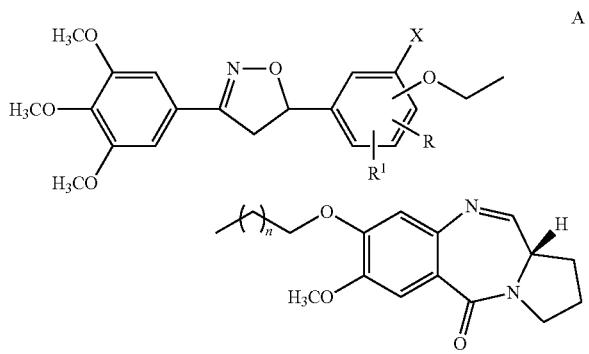

or a pharmaceutically acceptable salt thereof;
wherein R is H, 4-OCH$_3$, or 3-OCH$_3$;
R$^1$ is H, 5-H, or 5-OCH$_3$; and
X is H or OCH$_3$.
2. A compound of a formula

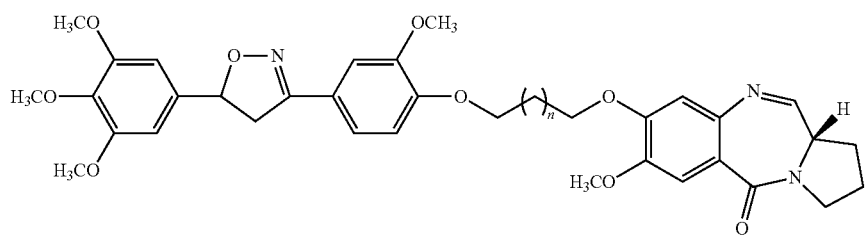

wherein n is 1, 2, 3, or 4; or

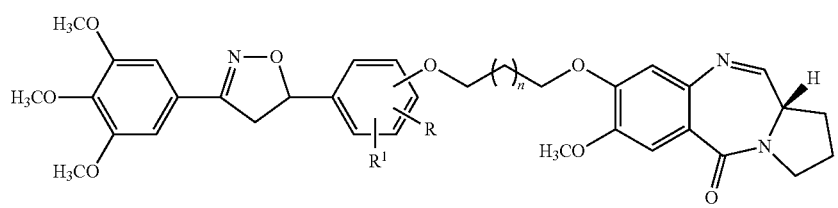

or a pharmaceutically acceptable salt thereof;
wherein R is 4-OCH$_3$ or 3-OCH$_3$;
R$^1$ is 5-H or 5-OCH$_3$; and
n is 1, 2, 3, or 4.

3. The compound of claim 2, wherein the compound is
(11aS)-7-(methyloxy)-8-(3-[(2-(methyloxy)-4-5-[3,4,5-tri(methyloxy)phenyl]-4,5-dihydro-3-isoxazolylphenyl)oxy]propyloxy)-2,3,5,11a-tetrahydro-1H benzo[e]pyrrolo[1,2-a][1,4]diazepi-5-one;
(11aS)-7-(methyloxy)-8-(4-[(2-(methyloxy)-4-5-[3,4,5-tri(methyloxy)phenyl]-4,5-dihydro-3-isoxazolylphenyl)oxy]butyloxy)-2,3,5,11a-tetrahydro-1H benzo[e]pyrrolo[1,2-a][1,4]diazepin-5-one;
(11aS)-7-(methyloxy)-8-(5-[(2-(methyloxy)-4-5-[3,4,5-tri(methyloxy)phenyl]-4,5-dihydro-3-isoxazolylphenyl)oxy]pentyloxy)-2,3,5,11a-tetrahydro-1H benzo[e]pyrrolo[1,2-a][1,4]diazepi-5-one;
(11aS)-7-(methyloxy)-8-(6-[(2-(methyloxy)-4-5-[3,4,5-tri(methyloxy)phenyl]-4,5-dihydro-3-isoxazolylphenyl)oxy]hexyloxy)-2,3,5,11a-tetrahydro-1H benzo[e]pyrrolo[1,2-a][1,4]diazepi-5-one;
(11aS)-7-(methyloxy)-8-(3-[(2-(methyloxy)-5-3-[2,3,4-tri(methyloxy)phenyl]-4,5-dihydro-5-isoxazolylphenyl)oxy]propyloxy)-2,3,5,11a-tetrahydro-1H-benzo[e]pyrrolo[1,2-a][1,4]diazepin-5-one;
(11aS)-7-(methyloxy)-8-(4-[(2-(methyloxy)-5-3-[2,3,4-tri(methyloxy)phenyl]-4,5-dihydro-5-isoxazolylphenyl)oxy]butyloxy)-2,3,5,11a-tetrahydro-1H-benzo[e]pyrrolo[1,2-a][1,4]diazepin-5-one;
(11aS)-7-(methyloxy)-8-(5-[(2-(methyloxy)-5-3-[2,3,4-tri(methyloxy)phenyl]-4,5-dihydro-5-isoxazolylphenyl)oxy]pentyloxy)-2,3,5,11a-tetrahydro-1H-benzo[e]pyrrolo[1,2-a][1,4]diazepin-5-one;
(11aS)-7-(methyloxy)-8-(6-[(2-(methyloxy)-5-3-[2,3,4-tri(methyloxy)phenyl]-4,5-dihydro-5-isoxazolylphenyl)oxy]hexyloxy)-2,3,5,11a-tetrahydro-1H-benzo[e]pyrrolo[1,2-a][1,4]diazepin-5-one;
(11aS)-8-(3-[(2,6-di(methyloxy)-4-3-[2,3,4-tri(methyloxy)phenyl]-4,5-dihydro-5-isoxazolylphenyl)oxy]propyloxy)-7-(methyloxy)-2,3,5,11a-tetrahydro-1H-benzo[e]pyrrolo[1,2-a][1,4]diazepin-5-one;
(11aS)-8-(4-[(2,6-di(methyloxy)-4-3-[2,3,4-tri(methyloxy)phenyl]-4,5-dihydro-5-isoxazolylphenyl)oxy]butyloxy)-7-(methyloxy)-2,3,5,11a-tetrahydro-1H-benzo[e]pyrrolo[1,2-a][1,4]diazepin-5-one;
(11aS)-8-(5-[(2,6-di(methyloxy)-4-3-[2,3,4-tri(methyloxy)phenyl]-4,5-dihydro-5-isoxazolylphenyl)oxy]pentyloxy)-7-(methyloxy)-2,3,5,11a-tetrahydro-1H-benzo[e]pyrrolo[1,2-a][1,4]diazepin-5-one; or
(11aS)-8-(6-[(2,6-di(methyloxy)-4-3-[2,3,4-tri(methyloxy)phenyl]-4,5-dihydro-5-isoxazolylphenyl)oxy]hexyloxy)-7-(methyloxy)-2,3,5,11a-tetrahydro-1H-benzo[e]pyrrolo[1,2-a][1,4]diazepin-5-one.

4. The compound of claim 2, wherein the compound is

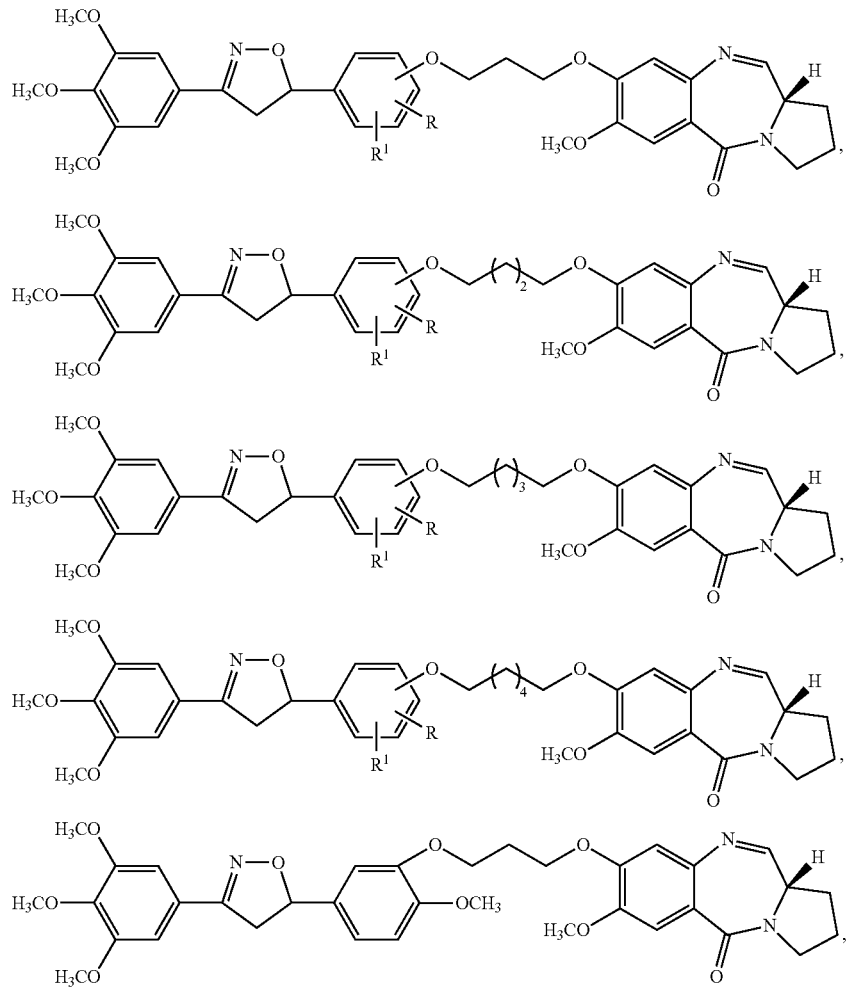

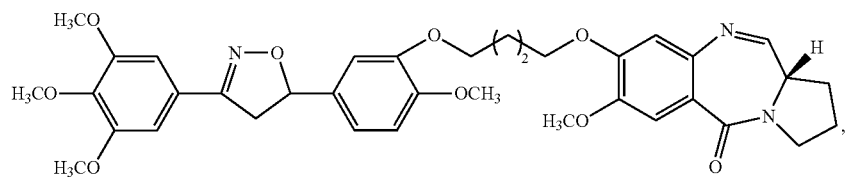
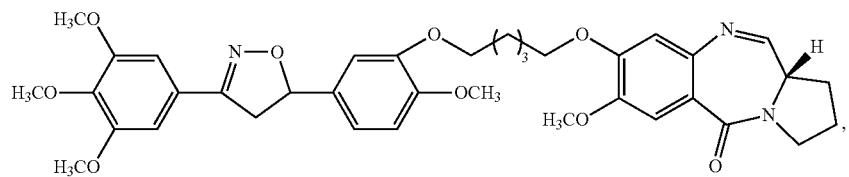
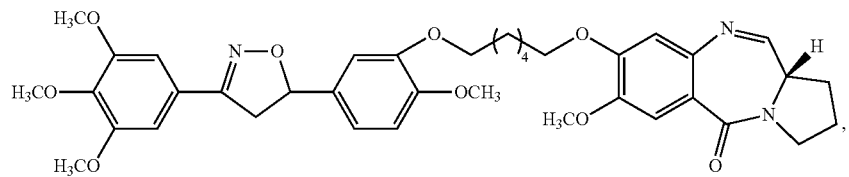
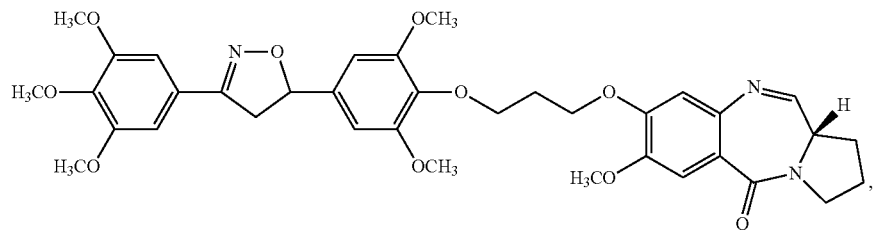
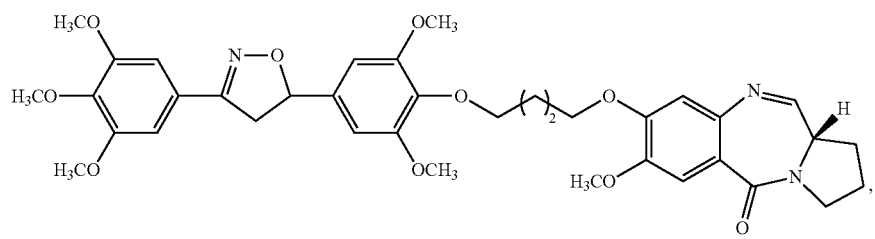
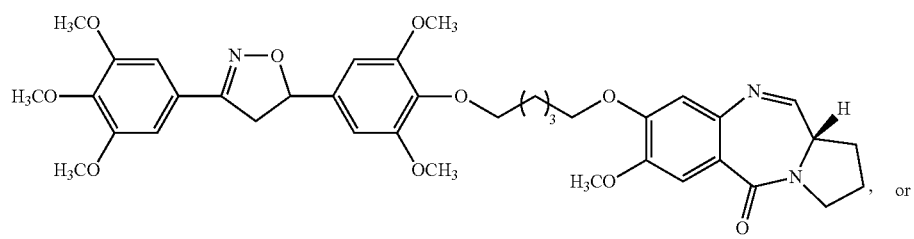

-continued

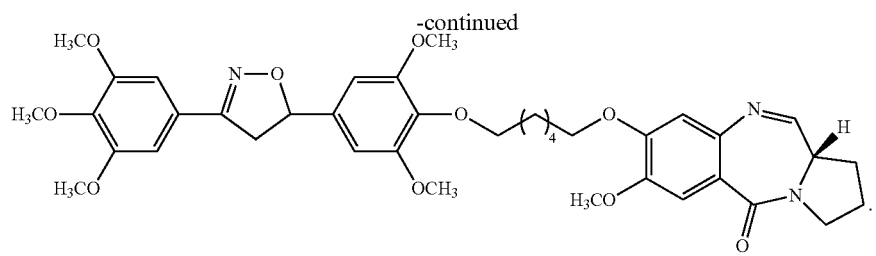

5. A method of reducing cancer/tumor activity of a human cancer cell line comprising:
mixing compound 5, compound 9, or compound 5 and compound 9 of claim 2 and a human cancer cell line is a lung cell line (Hop-62, NCI-H226, NCI-H522), a leukemia cell line (K-562, SR), a colon cell line (HCT-116, HCT-15, HCC-2998), a CNS cell line (SF-539), a melanoma cell line (SK-MEL-5, UACC-62, M14), a ovarian cell line (IGROV1), a renal cell line (A498), a prostate cell line (PC3), or a breast cell line (BT-549, MDA-MB-435, HS578T); and
reducing cancer/tumor activity of the human cancer cell line.

6. The method of claim 5 wherein compound 5 and compound 9 have a concentration when used for in vitro activity against leukemia for GI50 in the range of 0.12 to 0.24 µM and 1.12 to 1.90 µM respectively, at an exposure period of at least 48 hrs.

7. The method of claim 5 wherein compound 5 and compound 9 have a concentration when used for in vitro activity against lung for GI50 in the range of 0.12 to 0.46 µM and 0.61 to 3.68 µM respectively, at an exposure period of at least 48 hrs.

8. The method of claim 5 wherein compound 5 and compound 9 have a concentration when used for in vitro activity against colon for GI50 in the range 0.18 to 0.36 µM and 1.55 to 2.75 µM respectively, at an exposure period of at least 48 hrs.

9. The method of claim 5 wherein compound 5 and compound 9 have a concentration when used for in vitro activity against CNS for GI50 in the range of 0.22 to 0.34 µM and 1.71 to 1.96 µM respectively, at an exposure period of at least 48 hrs.

10. The method of claim 5 wherein compound 5 and compound 9 have a concentration when used for in vitro activity against melanoma for GI50 in the range of 0.16 to 0.27 µM and 1.47 to 2.88 µM respectively, at an exposure period of at least 48 hrs.

11. The method of claim 5 wherein compound 5 and compound 9 have a concentration when used for in vitro activity against ovarian for GI50 in the range of 0.24 to 0.47 µM and 1.57 to 3.37 µM respectively, at an exposure period of at least 48 hrs.

12. The method of claim 5 wherein compound 5 and compound 9 have a concentration when used for in vitro activity against renal for GI50 in the range of 0.18 to 0.30 µM and 1.39 to 3.51 µM respectively, at an exposure period of at least 48 hrs.

13. The method of claim 5 wherein compound 5 and compound 9 have a concentration when used for in vitro activity against prostate for GI50 in the range of 0.32 to 0.33 µM and 0.58 to 2.48 µM respectively, at an exposure period of at least 48 hrs.

14. The method of claim 5 wherein compound 5 and compound 9 have a concentration when used for in vitro activity against breast for IC50 in the range 0.09 to 0.28 µM and 1.10 to 3.54 µM respectively, at an exposure period of at least 48 hrs.

15. A pharmaceutical composition comprising a compound of claim 1 or a pharmaceutically acceptable salt thereof mixed with pharmaceutically acceptable carriers, adjuvants and additives.

16. A pharmaceutical composition as claimed in claim 15, wherein the compound used is represented by a formula

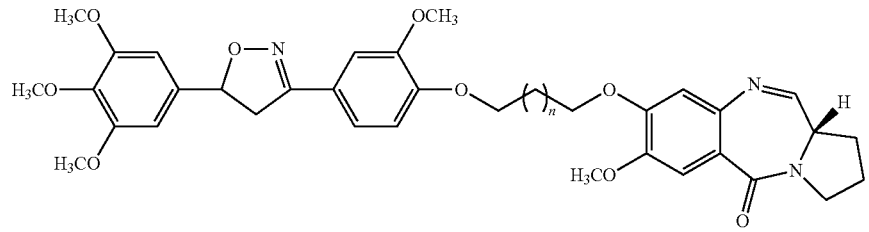

wherein n is 1, 2, 3, or 4; or

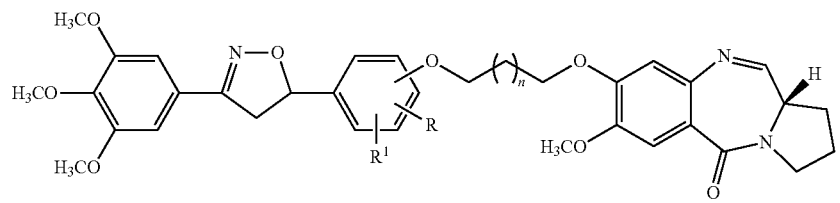

wherein R is 4-OCH₃ or 3-OCH₃;
R¹ is 5-H or 5-OCH₃; and
n is 1, 2, 3, or 4.

17. A process for the preparation of a compound of claim 2, the process comprising the steps of:

a) reacting (2S)—N-[4-(n-bromoalkyl)oxy-5-methoxy-2-nitrobenzoyl]pyrrolidine-2-carboxaldehyde diethylthioacetal of formula 1

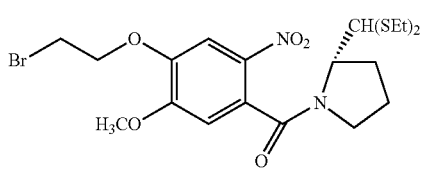

with a compound of formula 2 or 6

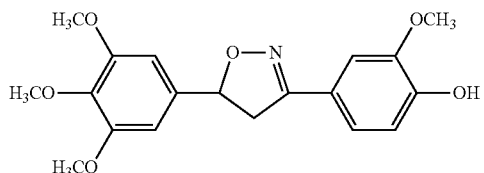

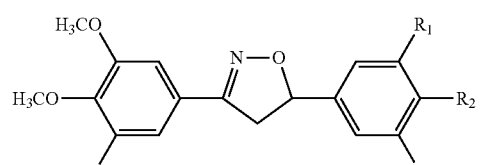

wherein R₁ is OH, R₂ is OCH₃, and R₃ is H or R₁ is OCH₃, R₂ is OH, and R₃ is OCH₃; in the presence of K₂CO₃, in an organic solvent, under refluxing temperature to obtain the resultant nitro compounds of formula 3a-d and 7a-h respectively,

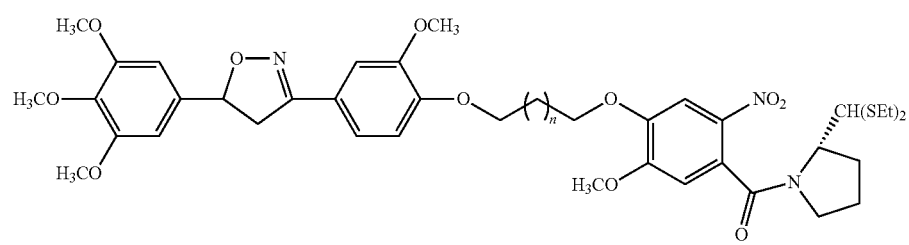

wherein n is 1, 2, 3, or 4;

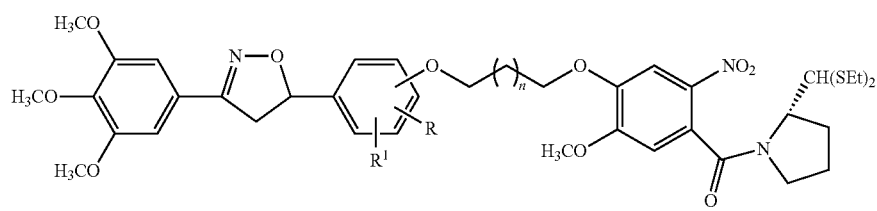

wherein R is 4-OCH₃ and R¹ is 5-H, or R is 3-OCH₃ and R¹ is 5-OCH₃; and
n is 1, 2, 3, or 4;

b) reducing the nitro compounds of formula 3a-d and 7a-h with SnCl₂.2H₂O, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired products of formula 4a-d and 8a-h,

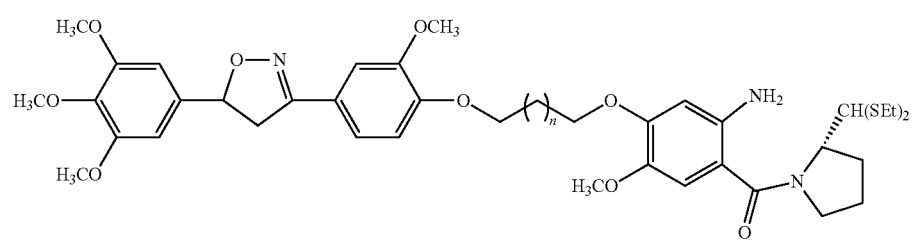

wherein n is 1, 2, 3, or 4;

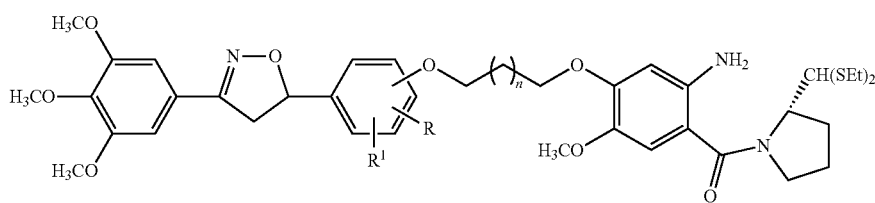

8a-h wherein R is 4-OCH₃ and R¹ is 5-H, or R is 3-OCH₃ and R¹ is 5-OCH₃; and
n is 1, 2, 3, or 4;
c) reacting amino compounds of formula 4 and 8 with mercuric chloride, in a mixture of water and organic solvent, in the presence of mild inorganic base, under stirring, at a temperature of about 20-30° C., for a period of 8-12 hrs, followed by the extraction of yellow organic supernatant and washing with sodium bicarbonate and brine, respectively, and evaporating the organic layer, under reduced pressure and further purified by column chromatography to obtain the desired product having a formula

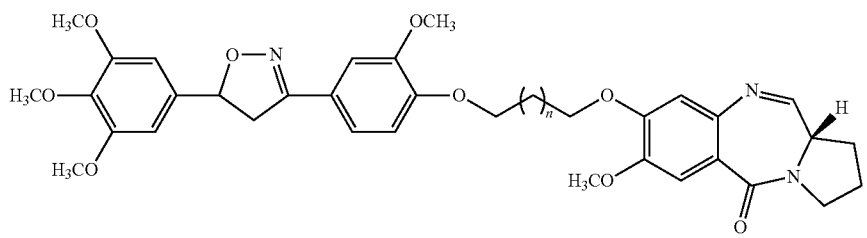

5 wherein n is 1, 2, 3, or 4; or

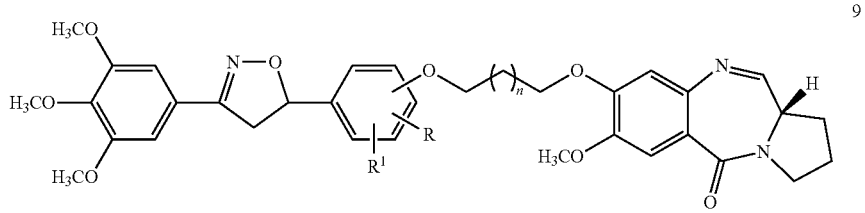

9 wherein R is 4-OCH₃ or 3-OCH₃;
R¹ is 5-H or 5-OCH₃; and
n=1, 2, 3, or 4.

18. A process as claimed in claim 17, wherein the mild inorganic base used in step (a) is potassium carbonate.

19. A process as claimed in claim 17, wherein the aprotic organic solvent used in step (a) is acetone and acetonitrile.

20. A process as claimed in claim 17, wherein the organic solvent used in step (c) is acetonitrile and acetone.

21. A process as claimed in claim 17, wherein the alcohol used in step (b) is methanol or ethanol.

22. A process as claimed in claim 17, wherein compound 5 and compound 9 are represented by:

(11aS)-7-(methyloxy)-8-(3-[(2-(methyloxy)-4-5-[3,4,5-tri(methyloxy)phenyl]-4,5-dihydro-3-isoxazolylphenyl)oxy]propyloxy)-2,3,5,11a-tetrahydro-1H benzo[e]pyrrolo[1,2-a][1,4]diazepi-5-one;

(11aS)-7-(methyloxy)-8-(4-[(2-(methyloxy)-4-5-[3,4,5-tri(methyloxy)phenyl]-4,5-dihydro-3-isoxazolylphenyl)oxy]butyloxy)-2,3,5,11a-tetrahydro-1H benzo[e]pyrrolo[1,2-a][1,4]diazepin-5-one;

(11aS)-7-(methyloxy)-8-(5-[(2-(methyloxy)-4-5-[3,4,5-tri(methyloxy)phenyl]-4,5-dihydro-3-isoxazolylphenyl)oxy]pentyloxy)-2,3,5,11a-tetrahydro-1H benzo[e]pyrrolo[1,2-a][1,4]diazepi-5-one;

(11aS)-7-(methyloxy)-8-(6-[(2-(methyloxy)-4-5-[3,4,5-tri(methyloxy)phenyl]-4,5-dihydro-3-isoxazolylphenyl)oxy]hexyloxy)-2,3,5,11a-tetrahydro-1H benzo[e]pyrrolo[1,2-a][1,4]diazepi-5-one;

(11aS)-7-(methyloxy)-8-(3-[(2-(methyloxy)-5-3-[2,3,4-tri(methyloxy)phenyl]-4,5-dihydro-5-isoxazolylphenyl)oxy]propyloxy)-2,3,5,11a-tetrahydro-1H-benzo[e]pyrrolo[1,2-a][1,4]diazepin-5-one;

(11aS)-7-(methyloxy)-8-(4-[(2-(methyloxy)-5-3-[2,3,4-tri(methyloxy)phenyl]-4,5-dihydro-5-isoxazolylphenyl)oxy]butyloxy)-2,3,5,11a-tetrahydro-1H-benzo[e]pyrrolo[1,2-a][1,4]diazepin-5-one;

(11aS)-7-(methyloxy)-8-(5-[(2-(methyloxy)-5-3-[2,3,4-tri(methyloxy)phenyl]-4,5-dihydro-5-isoxazolylphenyl)oxy]pentyloxy)-2,3,5,11a-tetrahydro-1H-benzo[e]pyrrolo[1,2-a][1,4]diazepin-5-one;

(11aS)-7-(methyloxy)-8-(6-[(2-(methyloxy)-5-3-[2,3,4-tri(methyloxy)phenyl]-4,5-dihydro-5-isoxazolylphenyl)oxy]hexyloxy)-2,3,5,11a-tetrahydro-1H-benzo[e]pyrrolo[1,2-a][1,4]diazepin-5-one;

(11aS)-8-(3-[(2,6-di(methyloxy)-4-3-[2,3,4-tri(methyloxy)phenyl]-4,5-dihydro-5-isoxazolylphenyl)oxy]propyloxy)-7-(methyloxy)-2,3,5,11a-tetrahydro-1H-benzo[e]pyrrolo[1,2-a][1,4]diazepin-5-one;

(11aS)-8-(4-[(2,6-di(methyloxy)-4-3-[2,3,4-tri(methyloxy)phenyl]-4,5-dihydro-5-isoxazolyl phenyl)oxy]butyloxy)-7-(methyloxy)-2,3,5,11a-tetrahydro-1H-benzo[e]pyrrolo[1,2-a][1,4]diazepin-5-one;

(11aS)-8-(5-[(2,6-di(methyloxy)-4-3-[2,3,4-tri(methyloxy)phenyl]-4,5-dihydro-5-isoxazolyl phenyl)oxy]pentyloxy)-7-(methyloxy)-2,3,5,11a-tetrahydro-1H-benzo[e]pyrrolo[1,2-a][1,4]diazepin-5-one; and (11aS)-8-(6-[(2,6-di(methyloxy)-4-3-[2,3,4-tri(methyloxy)phenyl]-4,5-dihydro-5-isoxazolyl phenyl)oxy]hexyloxy)-7-(methyloxy)-2,3,5,11a-tetrahydro-1H-benzo[e]pyrrolo[1,2-a][1,4]diazepin-5-one.

23. A pharmaceutical composition comprising a compound of claim 2 or a pharmaceutically acceptable salt thereof mixed with pharmaceutically acceptable carriers, adjuvants and additives.

* * * * *

UNITED STATES PATENT AND TRADEMARK OFFICE
CERTIFICATE OF CORRECTION

PATENT NO. : 8,372,831 B2
APPLICATION NO. : 12/934594
DATED : February 12, 2013
INVENTOR(S) : Ahmed et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 184 days.

Signed and Sealed this
Fifteenth Day of October, 2013

Teresa Stanek Rea
*Deputy Director of the United States Patent and Trademark Office*